(12) United States Patent
Mitsuhashi et al.

(10) Patent No.: US 7,440,103 B2
(45) Date of Patent: Oct. 21, 2008

(54) INSPECTION APPARATUS OF WIRING PATTERN, INSPECTION METHOD, DETECTION APPARATUS, DETECTION METHOD

(75) Inventors: Mitsuyuki Mitsuhashi, Kitakatsushika-gun (JP); Masao Saito, Soka (JP)

(73) Assignee: Toppan Printing Co., Ltd., Tokyo (JP)

( * ) Notice: Subject to any disclaimer, the term of this patent is extended or adjusted under 35 U.S.C. 154(b) by 453 days.

(21) Appl. No.: 11/117,422

(22) Filed: Apr. 29, 2005

(65) Prior Publication Data

US 2005/0190259 A1    Sep. 1, 2005

Related U.S. Application Data

(63) Continuation of application No. PCT/JP03/13854, filed on Oct. 29, 2003.

(30) Foreign Application Priority Data

Oct. 30, 2002  (JP) ............................ 2002-315833
Jun. 6, 2003  (JP) ............................ 2003-162861

(51) Int. Cl.
   *G01J 4/00*    (2006.01)

(52) U.S. Cl. ..................... 356/364; 356/368; 356/369

(58) Field of Classification Search .......... 356/364–369
   See application file for complete search history.

(56) References Cited

U.S. PATENT DOCUMENTS 6,690,469 B1 *  2/2004  Shibata et al. ............... 356/369
2001/0010363 A1  8/2001  Watanabe et al.

FOREIGN PATENT DOCUMENTS

| JP | 1-263540 | 10/1989 |
| JP | 4-289409 | 10/1992 |
| JP | 2000-155099 | 6/2000 |
| JP | 2001-281165 | 10/2001 |

OTHER PUBLICATIONS

Office Action issued in corresponding Chinese Patent Application No. 2003801024272; dated Apr. 11, 2008.

* cited by examiner

*Primary Examiner*—L. G Lauchman

(57) ABSTRACT

A wiring pattern inspection apparatus comprises a light source, a parallel light guiding section which guides light from the light source substantially in parallel, and a light extraction section which extracts a transverse wave light component crossing the light guiding direction at right angles from the light guided by the parallel light guiding section and which converts the transverse wave light component into a specific polarized component and which irradiates a work with the specific polarized component and which extracts a vertical wave light component from reflected light obtained by reflecting the emitted specific polarized component by the work.

26 Claims, 19 Drawing Sheets

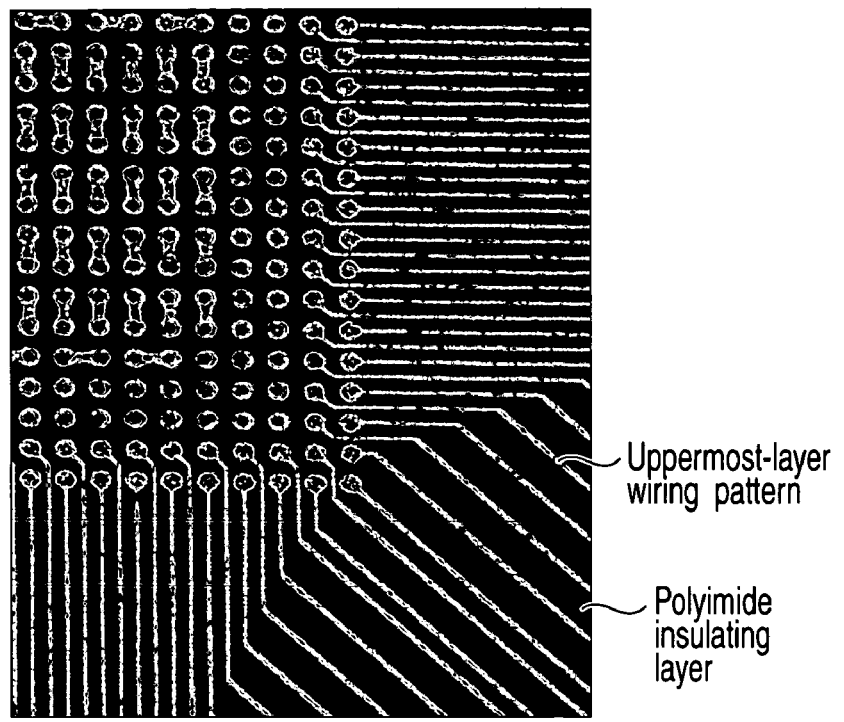
F I G. 6A
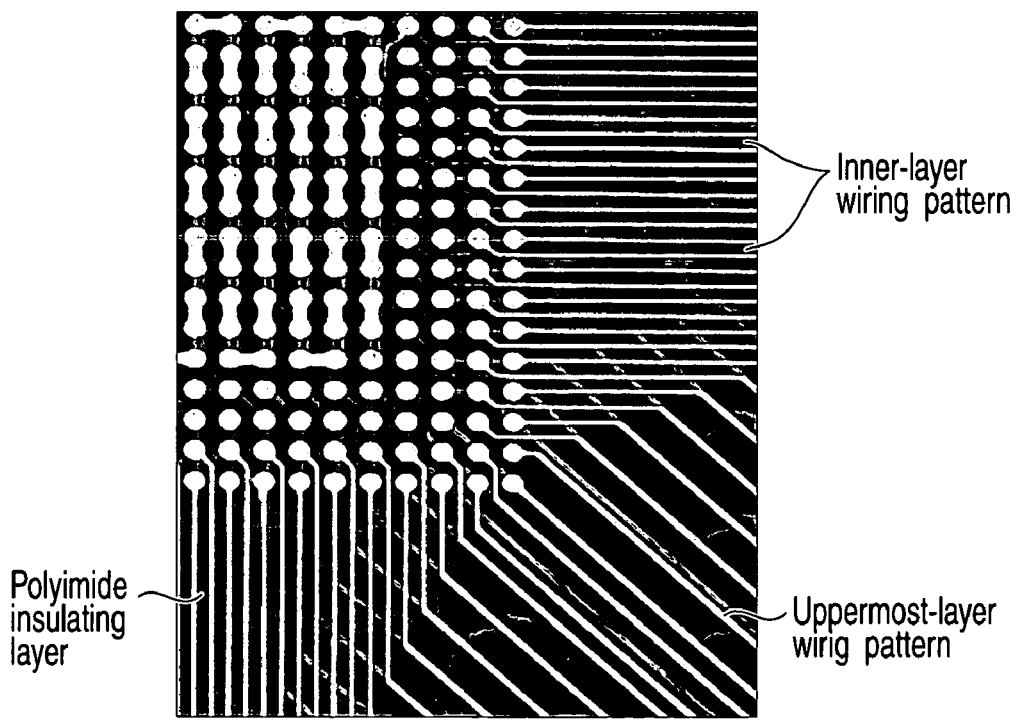
F I G. 6B

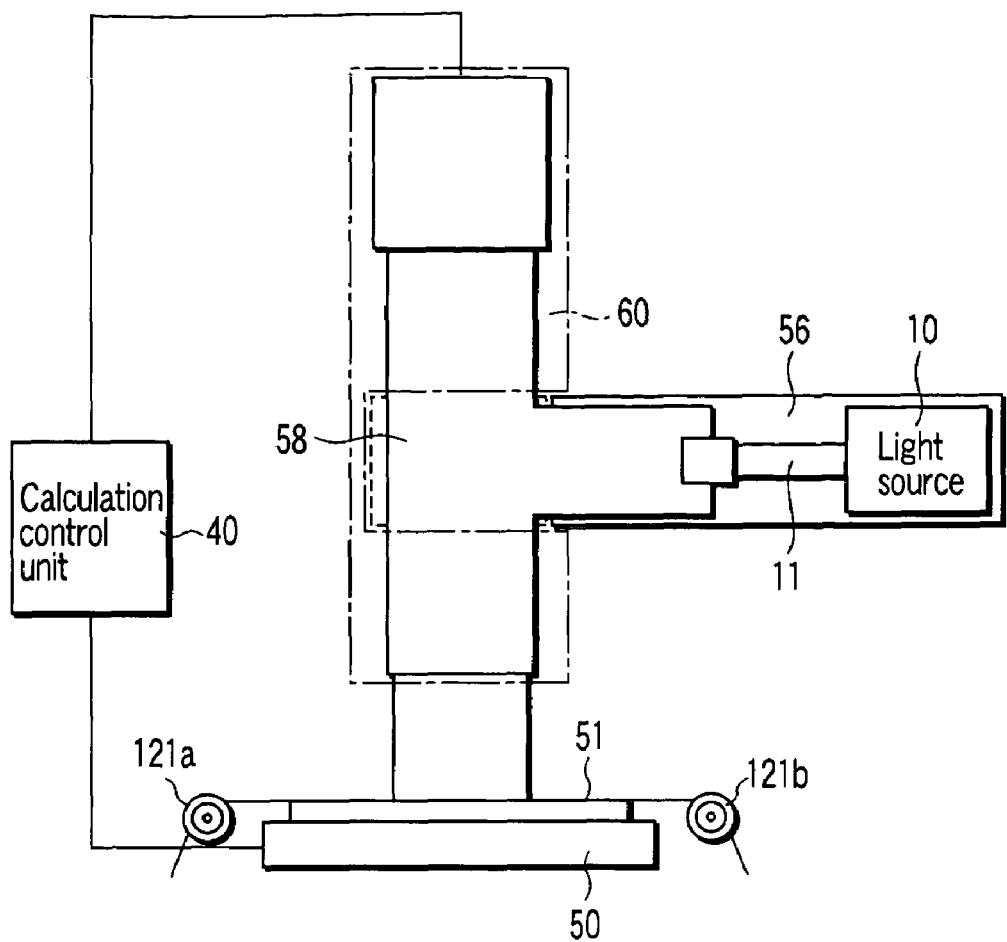
F I G. 13
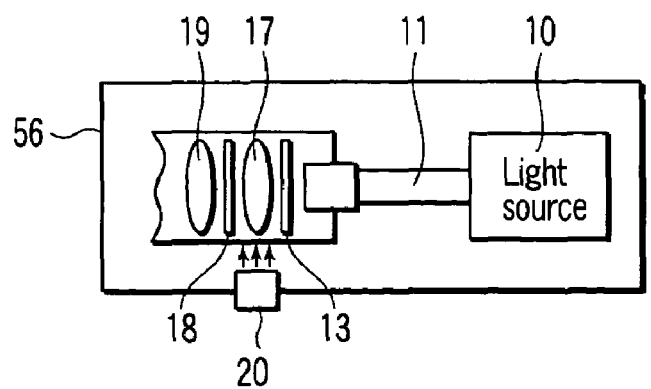
F I G. 14

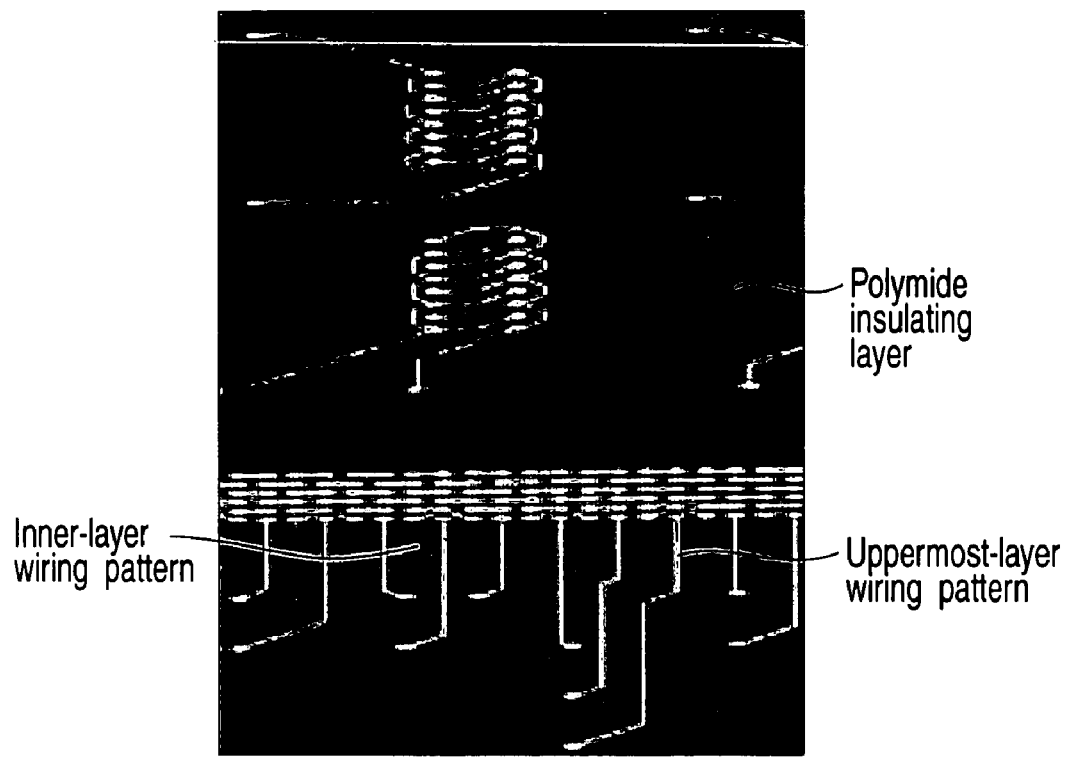
F I G. 18A
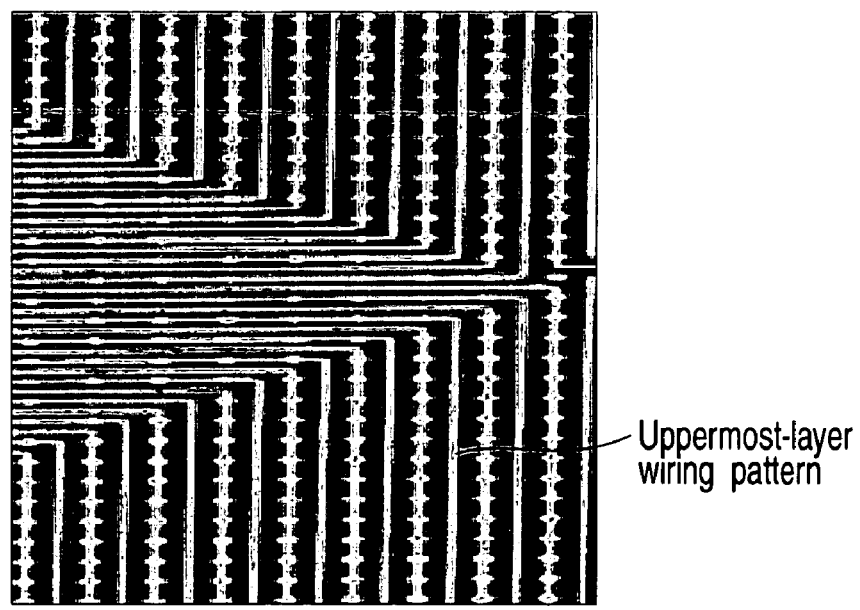
F I G. 18B

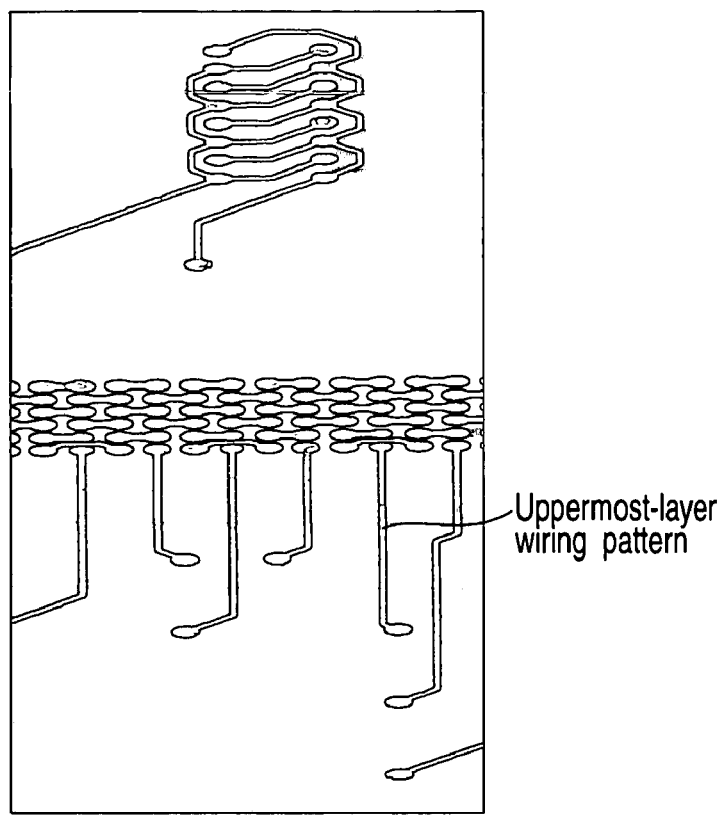
F I G. 19A
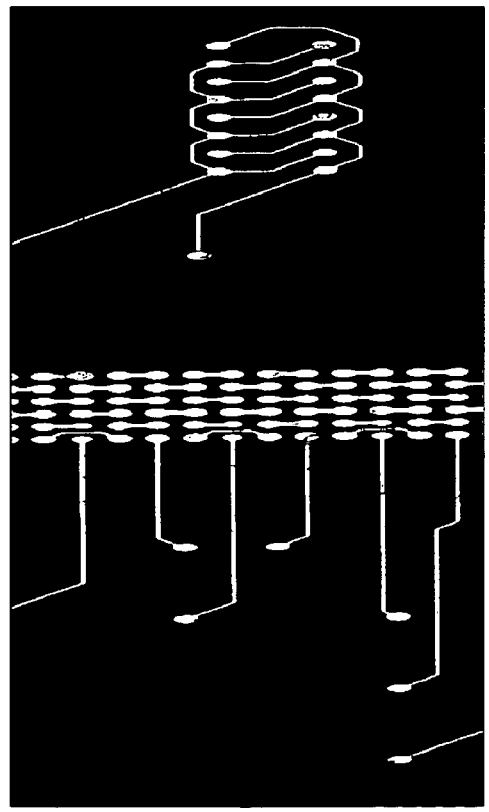
F I G. 19B

INSPECTION APPARATUS OF WIRING PATTERN, INSPECTION METHOD, DETECTION APPARATUS, DETECTION METHOD

CROSS REFERENCE TO RELATED APPLICATIONS

This is a Continuation Application of PCT Application No. PCT/JP03/13854, filed Oct. 29, 2003, which was published under PCT Article 21(2) in Japanese.

This application is based upon and claims the benefit of priority from prior Japanese Patent Applications No. 2002-315833, filed Oct. 30, 2002; and No. 2003-162861, filed Jun. 6, 2003, the entire contents of both of which are incorporated herein by reference.

BACKGROUND OF THE INVENTION

1. Field of the Invention

The present invention relates to an inspection apparatus of a wiring pattern, an inspection method, a detection apparatus, and a detection method for optically extracting a wiring pattern of an uppermost layer in a multilayered wiring substrate for a semiconductor package, on which a plurality of wiring patterns are stacked, for example, via a polyimide insulating layer having transparency, and picking up an image by high resolution to automatically inspect and detect the pattern.

2. Description of the Related Art

In general, in a wiring pattern formed on a multilayered wiring substrate for a semiconductor package for use in a purpose of making an electronic apparatus smaller or lighter, a copper foil is laminated on a polyimide film via an adhesive and patterned/treated by a subtractive process, a semi-additive process or the like, and a portion having a thickness of 5 to 15 μm, and a highest degree of integration has a width of about 10 μm.

In this pattering process step, there is a fear that severe defects are suddenly produced such as thinning (cracking) of the wiring pattern, breaking of wire, shorting, and thickening (protrusion). Therefore, the presence of these defects has heretofore been judged by an open-/short-circuit inspection or a visual inspection. However, the visual inspection raises the issue that skills are required with the miniaturization of the pattern, and fluctuation or defect oversight is caused in an inspection result by an inspector's physical condition or the like. Then, in recent years, various types of automatic inspection apparatuses have been proposed which automatically inspect the presence of defects using cameras (e.g., Jpn. Pat. Appln. KOKAI Publication No. 10-19531 (Example 1) and Jpn. Pat. No. 2962565 (FIGS. 5, 7)). Moreover, it is possible to visually inspect various types of defects existing in a wiring pattern having a minimum width of 10 μm in the multilayered wiring substrate for the semiconductor package, but there is the problem that much inspection time is required for the visual inspection, and product unit price increases accompanying an increase in personnel costs. Therefore, automatic inspection is required. For example, an imaging resolution of 1 μm has to be realized in order to detect ⅓ or more defects within the width of 10 μm. To solve the problem, an imaging method, an inspection method, further a handling method and the like need to be sought in a broad view of the relationship between the imaging resolution and imaging view field (object work size).

In general, in the automatic inspection apparatus which automatically inspects the presence of defects using cameras, a plurality of wiring patterns on the same work are imaged simultaneously, with a time difference, in divided areas or the like by a plurality of sensor cameras (line CCD device, area CCD device, etc.), and the image is recognized. By this process, defects are detected such as thinning (cracking), breaking of wire, shorting, thickening (protrusion) and the like existing in the wiring pattern. As the recognizing process, a method is general in which CAD data (pattern design information) or satisfactory work (work on which the wiring pattern is correctly formed) is registered as a reference master image in advance, and a portion having a difference is judged as a defect by methods such as a comparison process of this master image with an inspection image (inspection object pattern image), and a characteristic extraction process. At this time, the inspection image is reflected noting the wiring pattern formed on the uppermost layer, and the image is picked up without considering any influence of an inner-layer wiring pattern in most cases.

As examples of a reason for this, an inner-layer wiring pattern does not exist in a product, or the imaging of the uppermost-layer wiring pattern is not influenced by an insulating layer substrate type interposed between the wiring patterns, substrate thickness, substrate color, transmission/reflection spectral sensitivity and the like even in a product in which the inner-layer wiring pattern exists. Even when the inner-layer wiring pattern exists and exerts a slight influence, the influence can be easily eliminated by threshold value adjustment at imaging time, and it is not necessary to regard reflection influence of the inner-layer wiring pattern as an optical problem from the beginning.

However, in a case where the conventional inspection apparatus is used, in the multilayered wiring substrate for the semiconductor package, when the thickness of the polyimide film insulating layer interposed between the wiring patterns and having transparency is about 10 to 25 μm, and small, and attempts to image the uppermost-layer wiring pattern with a high resolution are made, the wiring pattern existing in the inner layer is reflected, and a clear pattern image cannot be obtained noting only the uppermost-layer wiring pattern.

Moreover, optical conditions are important for performing the above-described inspection using the image picked up by the camera. Unless the defect can be optically visualized, secure inspection is impossible even if the process algorithm is sophisticated.

Furthermore, it has also been proposed that fluorescent components generated from the insulating layer be detected using fluorescence illumination on the wiring pattern and insulating layer portion to thereby extract and inspect the wiring pattern portion in a pseudo manner. However, in this method, an image in which a wiring pattern edge is extracted in the pseudo manner is obtained by fluorescence emission. Therefore, defects such as pinholes in the wiring pattern and cracks existing on the top side of the wiring pattern cannot be detected. The wiring pattern needs to be noted and inspected in order to guarantee the quality of the multilayered wiring substrate for the semiconductor package. Therefore, it has been demanded that apparent quality guarantee be more firmly performed as a package inspection in such a manner that a copper wiring pattern can be directly seen, surface defects such as micro pinholes and dents, or quality of filled vias for performing interlayer connection can be observed, and high-speed signal transmission is realized. Moreover, when the inspection noting the wiring pattern can be performed, a manufacturing process is checked by monitoring good/bad points of the wiring pattern formed during the manufacturing, and control of a process state can be involved in order to keep the manufacturing process itself to be optimum.

Moreover, the invention described in Jpn. Pat. Appln. KOKAI Publication No. 10-19531 is an invention in which the wiring pattern is imaged as a dark image to thereby image the wiring pattern. Therefore, in the method described in Jpn. Pat. Appln. KOKAI Publication No. 10-19531, the wiring pattern can only be picked up as the dark image, and it is impossible to realize sophisticated imaging to such an extent that surface defects like the micro pinholes and dents, or filled via quality to perform interlayer connection can also be observed.

Furthermore, in the invention described in Jpn. Pat. No. 2962565, laser light having a specific wavelength (450 nm or less) is radiated, and the wiring pattern is picked up as a bright image utilizing a difference between a reflectance from the wiring pattern and that from a polyimide-based insulating film (ON AL). However, the usual CCD does not have any sensitivity with respect to light having a wavelength of 450 nm or less, and a special imaging system is required. On the other hand, as to the wavelength (e.g., around 550 nm) to which the usual CCD has sensitivity, there is little difference between the reflectance from the wiring pattern and that from the polyimide-based insulating film (ON AL). In the method disclosed in Jpn. Pat. No. 2962565, it is difficult to image only the wiring pattern of the uppermost layer and not to image the wiring pattern of the inner layer.

Moreover, in the automatic inspection of the wiring pattern, it is necessary to image the wiring pattern having a large area in a short time. However, the method disclosed in Jpn. Pat. No. 2962565 is so-called point scanning. In the method, the laser light is condensed to irradiate the wiring pattern, and the laser light with which the wiring pattern is irradiated is scanned to thereby image the wiring pattern. Therefore, much time is required. Further in the method disclosed in Jpn. Pat. No. 2962565, intensity of the laser light reflected in various directions on the wiring pattern is detected, and information such as an arrangement angle of the wiring pattern is obtained based on a detected value. Therefore, at least two detection systems need to be disposed, and the constitution is complicated. Furthermore, since the detected value from each system is calculated to thereby restore a wiring pattern state, the calculation amount is enormous.

BRIEF SUMMARY OF THE INVENTION

That is, according to a first aspect of the present invention, there is provided a wiring pattern detection apparatus which optically detects an uppermost-layer wiring pattern of a work comprising a multilayered wiring substrate for a semiconductor package having wiring patterns on at least front/back surfaces of a light-transmitting base film, the apparatus comprising: a light source; parallel light guiding means for guiding light from the light source substantially in parallel; first extraction means for extracting first linearly polarized light whose electric-field vector direction crosses a guiding direction of the light at right angles from the light guided by the parallel light guiding means; circularly polarized light conversion means for converting the first linearly polarized light extracted by the first extraction means into circularly polarized light; irradiation means for irradiating the work with the circularly polarized light converted by the circularly polarized light conversion means; second extraction means for extracting second linearly polarized light whose electric-field vector direction crosses the first linearly polarized light at right angles from reflected light obtained by reflecting the circularly polarized light emitted by the irradiation means by the work; and image pickup means for imaging the second linearly polarized light extracted by the second extraction means.

Therefore, when the above-described means are taken in the wiring pattern detection apparatus of the first aspect of the present invention, the light from the light source is converted into the circularly polarized light, and the work can be irradiated with this circularly polarized light. Furthermore, the second linearly polarized light can be extracted from the reflected light reflected by the irradiated work to pick up the image. This second linearly polarized light includes information on the uppermost-layer wiring pattern.

According to a second aspect of the present invention, there is provided a wiring pattern detection apparatus which optically detects an uppermost-layer wiring pattern of a work comprising a multilayered wiring substrate for a semiconductor package having wiring patterns on at least front/back surfaces of a light-transmitting base film, the apparatus comprising: a light source; parallel light guiding means for guiding light from the light source substantially in parallel; a polarized beam splitter to extract first linearly polarized light whose electric-field vector direction crosses a guiding direction of the light at right angles from the light guided by the parallel light guiding means and to guide the extracted first linearly polarized light in the light guiding direction and a direction crossing the direction of the electric-field vector of the first linearly polarized light at right angles; a quarter-wavelength plate which converts the first linearly polarized light guided by the polarized beam splitter into circularly polarized light; irradiation means for irradiating the work with the circularly polarized light converted by the quarter-wavelength plate; and image pickup means.

Moreover, the circularly polarized light emitted by the irradiation means is inverted by the work to reverse a rotation direction, and is thereafter transmitted through the quarter-wavelength plate, second linearly polarized light whose electric-field vector direction crosses the first linearly polarized light at right angles is extracted by the polarized beam splitter, and the extracted second linearly polarized light is imaged by the image pickup means.

Therefore, when the above-described means are taken in the wiring pattern detection apparatus of the second aspect of the present invention, the light from the light source is converted into the circularly polarized light by the quarter-wavelength plate, and the work can be irradiated with this circularly polarized light. Furthermore, the second linearly polarized light can be extracted from the reflected light reflected by the irradiated work by the quarter-wavelength plate and polarized beam splitter to pick up the image. This second linearly polarized light includes information on the uppermost-layer wiring pattern.

According to a third aspect of the present invention, there is provided a wiring pattern detection apparatus which optically detects an uppermost-layer wiring pattern of a work comprising a multilayered wiring substrate for a semiconductor package having wiring patterns on at least front/back surfaces of a light-transmitting base film, the apparatus comprising: a light source; parallel light guiding means for guiding light from the light source substantially in parallel; a first polarized beam splitter to extract first linearly polarized light whose electric-field vector direction crosses a guiding direction of the light at right angles from the light guided by the parallel light guiding means; a second polarized beam splitter which guides the first linearly polarized light extracted by the first polarized beam splitter in the light guiding direction and a direction crossing the direction of the electric-field vector of the first linearly polarized light at right angles; a quarter-wavelength plate which converts the first linearly polarized light guided by the second polarized beam splitter into circularly polarized light; irradiation means for irradiating the work with the circularly polarized light converted by the quarter-wavelength plate; and image pickup means.

Moreover, the circularly polarized light emitted by the irradiation means is reflected by the work to reverse a rotation direction, and is thereafter transmitted through the quarter-wavelength plate, second linearly polarized light whose electric-field vector direction crosses the first linearly polarized light at right angles is extracted by the second polarized beam splitter, and the extracted second linearly polarized light is imaged by the image pickup means.

Therefore, when the above-described means are taken in the wiring pattern detection apparatus of the third aspect of the present invention, the light from the light source is once converted into the first linearly polarized light, the first linearly polarized light is converted into the circularly polarized light by the quarter-wavelength plate, and the work can be irradiated with this circularly polarized light. Furthermore, the second linearly polarized light can be extracted from the reflected light reflected by the irradiated work to pick up the image. This second linearly polarized light includes information on the uppermost-layer wiring pattern.

According to a fourth aspect of the present invention, there is provided a wiring pattern detection apparatus which optically detects an uppermost-layer wiring pattern of a work comprising a multilayered wiring substrate for a semiconductor package having wiring patterns on at least front/back surfaces of a light-transmitting base film, the apparatus comprising: a light source; parallel light guiding means for guiding light from the light source substantially in parallel; a polarization plate to extract first linearly polarized light whose electric-field vector direction crosses a guiding direction of the light at right angles from the light guided by the parallel light guiding means; a polarized beam splitter which guides the first linearly polarized light extracted by the polarization plate in the light guiding direction and a direction crossing the direction of the electric-field vector of the first linearly polarized light at right angles; a quarter-wavelength plate which converts the first linearly polarized light guided by the polarized beam splitter into circularly polarized light; irradiation means for irradiating the work with the circularly polarized light converted by the quarter-wavelength plate; and image pickup means.

Moreover, the circularly polarized light emitted by the irradiation means is reflected by the work to reverse a rotation direction, and is thereafter transmitted through the quarter-wavelength plate, second linearly polarized light whose electric-field vector direction crosses the first linearly polarized light at right angles is extracted by the polarized beam splitter, and the extracted second linearly polarized light is imaged by the image pickup means.

Therefore, when the above-described means are taken in the wiring pattern detection apparatus of the fourth aspect of the present invention, the light from the light source is converted into the circularly polarized light by the polarization plate, polarized beam splitter, and quarter-wavelength plate, and the work can be irradiated with this circularly polarized light. Furthermore, the second linearly polarized light can be extracted from the reflected light reflected by the irradiated work to pick up the image. This second linearly polarized light includes information on the uppermost-layer wiring pattern.

According to a fifth aspect of the present invention, there is provided a wiring pattern detection apparatus which optically detects an uppermost-layer wiring pattern of a work comprising a multilayered wiring substrate for a semiconductor package having wiring patterns on at least front/back surfaces of a light-transmitting base film, the apparatus comprising: a light source; parallel light guiding means for guiding light from the light source substantially in parallel; first extraction means for extracting first linearly polarized light whose electric-field vector direction crosses a guiding direction of the light at right angles from the light guided by the parallel light guiding means; polarized component extraction means for obtaining a predetermined polarized component from the first linearly polarized light extracted by the first extraction means via a polarization plate having a predetermined angle; irradiation means for irradiating the work with the polarized component obtained by the polarized component extraction means; second extraction means for extracting second linearly polarized light whose electric-field vector direction crosses the first linearly polarized light at right angles from reflected light obtained by reflecting the polarized component emitted by the irradiation means by the work; and image pickup means for imaging the second linearly polarized light extracted by the second extraction means.

Therefore, when the above-described means are taken in the wiring pattern detection apparatus of the fifth aspect of the present invention, the light from the light source is converted into the polarized component, and the work can be irradiated with this polarized component. Furthermore, the second linearly polarized light can be extracted from the reflected light reflected by the irradiated work to pick up the image. This second linearly polarized light includes information on the uppermost-layer wiring pattern.

According to a sixth aspect of the present invention, there is provided a wiring pattern detection apparatus which optically detects an uppermost-layer wiring pattern of a work comprising a multilayered wiring substrate for a semiconductor package having wiring patterns on at least front/back surfaces of a light-transmitting base film, the apparatus comprising: a light source; parallel light guiding means for guiding light from the light source substantially in parallel; a polarized beam splitter to extract first linearly polarized light whose electric-field vector direction crosses a guiding direction of the light at right angles from the light guided by the parallel light guiding means and to guide the extracted first linearly polarized light in the light guiding direction and a direction crossing the direction of the electric-field vector of the first linearly polarized light at right angles; polarized component extraction means for obtaining a predetermined polarized component from the first linearly polarized light guided by the polarized beam splitter via a polarization plate having a predetermined angle; irradiation means for irradiating the work with the polarized component obtained by the polarized component extraction means; and image pickup means.

Moreover, second linearly polarized light whose electric-field vector direction crosses the first linearly polarized light at right angles is extracted from reflected light obtained by reflecting the polarized component emitted by the irradiation means by the work by the polarized beam splitter, and the extracted second linearly polarized light is imaged by the image pickup means.

Therefore, when the above-described means are taken in the wiring pattern detection apparatus of the sixth aspect of the present invention, the light from the light source is converted into the polarized component, and the work can be irradiated with this polarized component. Furthermore, the second linearly polarized light can be extracted from the reflected light reflected by the irradiated work to pick up the image. This second linearly polarized light includes information on the uppermost-layer wiring pattern.

According to a seventh aspect of the present invention, there is provided a wiring pattern detection apparatus which optically detects an uppermost-layer wiring pattern of a work comprising a multilayered wiring substrate for a semiconductor package having wiring patterns on at least front/back surfaces of a light-transmitting base film, the apparatus comprising: a light source; parallel light guiding means for guiding light from the light source substantially in parallel; a first polarized beam splitter to extract first linearly polarized light whose electric-field vector direction crosses a guiding direction of the light at right angles from the light guided by the parallel light guiding means; a second polarized beam splitter which guides the first linearly polarized light extracted by the first polarized beam splitter in the light guiding direction and a direction crossing the direction of the electric-field vector of the first linearly polarized light at right angles; polarized component extraction means for obtaining a predetermined polarized component from the first linearly polarized light guided by the second polarized beam splitter via a polarization plate having a predetermined angle; irradiation means for irradiating the work with the polarized component obtained by the polarized component extraction means; and image pickup means.

Moreover, second linearly polarized light whose electric-field vector direction crosses the first linearly polarized light at right angles is extracted from reflected light obtained by reflecting the polarized component emitted by the irradiation means by the work by the second polarized beam splitter, and the extracted second linearly polarized light is imaged by the image pickup means.

Therefore, when the above-described means are taken in the wiring pattern detection apparatus of the seventh aspect of the present invention, the light from the light source is once converted into the first linearly polarized light, the first linearly polarized light is converted into the polarized component, and the work can be irradiated with this polarized component. Furthermore, the second linearly polarized light can be extracted from the reflected light reflected by the irradiated work to pick up the image. This second linearly polarized light includes information on the uppermost-layer wiring pattern.

According to an eighth aspect of the present invention, there is provided a wiring pattern detection apparatus which optically detects an uppermost-layer wiring pattern of a work comprising a multilayered wiring substrate for a semiconductor package having wiring patterns on at least front/back surfaces of a light-transmitting base film, the apparatus comprising: a light source; parallel light guiding means for guiding light from the light source substantially in parallel; a polarization plate to extract first linearly polarized light whose electric-field vector direction crosses a guiding direction of the light at right angles from the light guided by the parallel light guiding means; a polarized beam splitter to guide the first linearly polarized light extracted by the polarization plate in the light guiding direction and a direction crossing the direction of the electric-field vector of the first linearly polarized light at right angles; polarized component extraction means for obtaining a predetermined polarized component from the first linearly polarized light guided by the polarized beam splitter via the polarization plate having a predetermined angle; irradiation means for irradiating the work with the polarized component obtained by the polarized component extraction means; and image pickup means.

Moreover, second linearly polarized light crossing the first linearly polarized light at right angles is extracted from reflected light obtained by reflecting the polarized component emitted by the irradiation means by the work, and the extracted second linearly polarized light is imaged by the image pickup means.

Therefore, when the above-described means are taken in the wiring pattern detection apparatus of the eighth aspect of the present invention, the light from the light source is converted into the polarized component, and the work can be irradiated with this polarized component. Furthermore, the second linearly polarized light can be extracted from the reflected light reflected by the irradiated work to pick up the image. This second linearly polarized light includes information on the uppermost-layer wiring pattern.

According to a ninth aspect of the present invention, in the wiring pattern detection apparatus according to any one of first to eighth aspects, the image pickup means comprises a line sensor which continuously images a predetermined linear region in the work and which connects the continuously imaged linear regions to one another to thereby image a planar region of the work.

Therefore, when the above-described means are taken in the wiring pattern detection apparatus of the ninth aspect of the present invention, the work can be line-scanned to thereby pick up the image, and therefore the image can be picked up in a short time as compared with the work is point-scanned.

According to a tenth aspect of the present invention, in the wiring pattern detection apparatus according to any one of the first to eighth aspects, the parallel light guiding means comprises: a light guide which guides the light from the light source; a diffusion plate which diffuses the light from the light source while keeping an intensity distribution to be constant; paralleling means for bringing the light diffused by the diffusion plate substantially in parallel; and means for guiding the parallel light brought by the paralleling means.

Therefore, when the above-described means are taken in the wiring pattern detection apparatus of the tenth aspect of the present invention, the light from the light source can be diffused while keeping the intensity distribution to be constant, the image can be picked up with high resolution entirely without any unevenness.

According to an eleventh aspect of the present invention, in the wiring pattern detection apparatus of the tenth aspect, an infrared filter which removes an infrared component from the light from the light source is disposed between the light source and the light guide, or between the light guide and the diffusion plate.

Therefore, when the above-described means are taken in the wiring pattern detection apparatus of the eleventh aspect of the present invention, an infrared ray constituting a heat source can be cut in such a manner as to be prevented from being brought into the parallel light guiding means, and therefore temperature rise of the parallel light guiding means can be inhibited.

According to a twelfth aspect of the present invention, the wiring pattern detection apparatus according to any one of the first to eighth aspects further comprises: cooling means for cooling the parallel light guiding means.

Therefore, when the above-described means are taken in the wiring pattern detection apparatus of the twelfth aspect of the present invention, the parallel light guiding means can be cooled.

According to a thirteenth aspect of the present invention, the wiring pattern detection apparatus according to any one of the first to eighth aspects further comprises: selection means for selecting a wavelength region in which a difference between an amount of the uppermost-layer wiring pattern by reflected light and that of a pattern other than the uppermost-layer wiring pattern by the reflected light is larger than a predetermined value in the second linearly polarized light; and selected wavelength light component guiding means for guiding a light component in the wavelength region selected by the selection means.

Therefore, the above-described means are taken in the wiring pattern detection apparatus of the thirteenth aspect of the present invention, and accordingly the wavelength region in which the difference between the amount of the uppermost-layer wiring pattern by the reflected light and that of the pattern other than the uppermost-layer wiring pattern by the reflected light is larger than the predetermined value is selected in the second linearly polarized light, and an image constituted of the light component in the selected wavelength region can be picked up. Consequently, the image visualized into the uppermost-layer wiring pattern can be obtained.

According to a fourteenth aspect of the present invention, in the wiring pattern detection apparatus of the thirteenth aspect, the selected wavelength light component guiding means comprises one or two or more lenses which guide the light component in the wavelength region selected by the selection means in parallel with the image pickup means.

Therefore, when the above-described means are taken in the wiring pattern detection apparatus of the fourteenth aspect of the present invention, the light component of the selected wavelength region can be guided in parallel with the image pickup means appropriately using one or two or more lenses. As a result, a fine image visualized into the uppermost-layer wiring pattern can be picked up.

According to a fifteenth aspect of the present invention, in the wiring pattern detection apparatus according to the thirteenth aspect of the present invention, the base film is formed of a polyimide resin, the wiring pattern is formed of copper, the selection means selects a wavelength region including 550 nm, and the image pickup means comprises a CCD.

Therefore, the above-described means are taken in the wiring pattern detection apparatus of the fifteenth aspect of the present invention, and accordingly the uppermost-layer wiring pattern concerning the work formed of polyimide resin and copper which are typical materials of the base film and wiring pattern can be detected with good precision.

According to a sixteenth aspect of the present invention, in the wiring pattern detection apparatus of any one of the first to fourth aspects, the work is irradiated with elliptically polarized light instead of the circularly polarized light.

Therefore, when the above-described means are taken in the wiring pattern detection apparatus of the sixteenth aspect of the present invention, the work can be irradiated with not only the circularly polarized light but also the elliptically polarized light.

According to a seventeenth aspect of the present invention, in the wiring pattern detection apparatus of any one of the first to eighth aspects, the light source comprises a white light source.

Therefore, when the above-described means are taken in the wiring pattern detection apparatus of the seventeenth aspect of the present invention, the white light source is usable as the light source without using any special light source.

According to an eighteenth aspect of the present invention, there is provided a wiring pattern inspection apparatus comprising: inspection means for collating an image picked up by the image pickup means of the wiring pattern detection apparatus according to any one of the first to eighth aspects with a predetermined satisfactory image to inspect whether or not the uppermost-layer wiring pattern is satisfactory.

Therefore, when the above-described means are taken in the wiring pattern inspection apparatus of the eighteenth aspect of the present invention, it can be inspected with good precision whether or not the uppermost-layer wiring pattern is satisfactory.

According to a nineteenth aspect of the present invention, there is provided a wiring pattern detection method which optically detects an uppermost-layer wiring pattern of a work comprising a multilayered wiring substrate for a semiconductor package having wiring patterns on at least front/back surfaces of a light-transmitting base film, the method comprising: a parallel light guiding step of guiding light substantially in parallel; a first extraction step of extracting first linearly polarized light whose electric-field vector direction crosses a guiding direction of the light at right angles from the light guided by the parallel light guiding step; a circularly polarized light conversion step of converting the first linearly polarized light extracted by the first extraction step into circularly polarized light; an irradiation step of irradiating the work with the circularly polarized light converted by the circularly polarized light conversion step; a second extraction step of extracting second linearly polarized light whose electric-field vector direction crosses the first linearly polarized light at right angles from reflected light obtained by reflecting the circularly polarized light emitted by the irradiation step by the work; and an image pickup step of imaging the second linearly polarized light extracted by the second extraction step.

When the above-described means are taken in the wiring pattern detection method of the nineteenth aspect of the present invention, the light from the light source is converted into the circularly polarized light, and the work can be irradiated with the circularly polarized light. Furthermore, the second linearly polarized light can be extracted from the reflected light reflected by the irradiated work, and imaged. This second linearly polarized light includes information on the uppermost-layer wiring pattern.

According to a twentieth aspect of the present invention, there is provided a wiring pattern detection method which optically detects an uppermost-layer wiring pattern of a work comprising a multilayered wiring substrate for a semiconductor package having wiring patterns on at least front/back surfaces of a light-transmitting base film, the method comprising: parallel light guiding means for guiding light substantially in parallel; a step of extracting first linearly polarized light whose electric-field vector direction crosses a guiding direction of the light at right angles from the light guided by the parallel light guiding means by a polarization plate; a step of guiding the first linearly polarized light extracted by the polarization plate in the light guiding direction and a direction crossing the direction of the electric-field vector of the first linearly polarized light at right angles using a polarized beam splitter; a step of converting the first linearly polarized light guided by the polarized beam splitter into circularly polarized light by a quarter-wavelength plate; a step of irradiating the work with the circularly polarized light converted by the quarter-wavelength plate; and a step of reflecting the circularly polarized light emitted to the work by the work to reverse a rotation direction, thereafter transmitting the polarized light through the quarter-wavelength plate, and extracting second linearly polarized light which crosses the first linearly polarized light at right angles by the polarized beam splitter to image the extracted second linearly polarized light.

Therefore, when the above-described means are taken in the wiring pattern detection method of the twentieth aspect of the present invention, the light from the light source is converted into the circularly polarized light by the polarization plate, polarized beam splitter, and quarter-wavelength plate, and the work can be irradiated with the circularly polarized light. Furthermore, the second linearly polarized light can be extracted from the reflected light reflected by the irradiated work, and imaged. This second linearly polarized light includes information on the uppermost-layer wiring pattern.

According to a twenty-first aspect of the present invention, there is provided a wiring pattern detection method which optically detects an uppermost-layer wiring pattern of a work comprising a multilayered wiring substrate for a semiconductor package having wiring patterns on at least front/back surfaces of a light-transmitting base film, the method comprising: a parallel light guiding step of guiding light substantially in parallel; a first extraction step of extracting first linearly polarized light whose electric-field vector direction crosses a guiding direction of the light at right angles from the light guided by the parallel light guiding step; a polarized component extraction step of obtaining a predetermined polarized component from the first linearly polarized light extracted by the first extraction step via a polarization plate having a predetermined angle; an irradiation step of irradiating the work with the polarized component obtained by the polarized component extraction step; a second extraction step of extracting second linearly polarized light whose electric-field vector direction crosses the first linearly polarized light at right angles from reflected light obtained by reflecting the polarized component emitted by the irradiation step by the work; and an image pickup step of imaging the second linearly polarized light extracted by the second extraction step.

Therefore, when the above-described means are taken in the wiring pattern detection method of the twenty-first aspect of the present invention, the light from the light source is converted into the polarized component, and the work can be irradiated with the polarized component. Furthermore, the second linearly polarized light can be extracted from the reflected light reflected by the irradiated work, and imaged. This second linearly polarized light includes information on the uppermost-layer wiring pattern.

According to a twenty-second aspect of the present invention, in the wiring pattern detection method of any one of the nineteenth to twenty-first aspects, a predetermined linear region in the work is continuously imaged using a line sensor, and the continuously imaged linear regions are connected to one another to thereby image a planar region of the work.

Therefore, when the above-described means are taken in the wiring pattern detection method of the twenty-second aspect of the present invention, the work can be line-scanned to thereby pick up the image, and therefore the image can be picked up in a short time as compared with the work is point-scanned.

According to a twenty-third aspect of the present invention, in the wiring pattern detection method of any one of the nineteenth to twenty-first aspects, the parallel light guiding step comprises: a diffusion step of diffusing the light while keeping an intensity distribution to be constant; a paralleling step of bringing the light diffused by the diffusion step substantially in parallel; and a step of guiding the parallel light brought by the paralleling step.

Therefore, when the above-described means are taken in the wiring pattern detection method of the twenty-third aspect of the present invention, the light from the light source can be diffused while keeping the intensity distribution to be constant, the image can be picked up with high resolution entirely without any unevenness.

According to a twenty-fourth aspect of the present invention, in the wiring pattern detection method of the twenty-third aspect of the present invention, the parallel light guiding step further comprises: an infrared removing step of removing an infrared component from the light before the diffusion step.

Therefore, when the above-described means are taken in the wiring pattern detection apparatus of the twenty-fourth aspect of the present invention, an infrared ray constituting a heat source can be cut in such a manner as to be prevented from being brought into the parallel light guiding means, and therefore temperature rise of a light guiding member can be inhibited.

According to a twenty-fifth aspect of the present invention, the wiring pattern detection method of any one of the nineteenth to twenty-first aspects further comprises: a selection step of selecting a wavelength region in which a difference between an amount of the uppermost-layer wiring pattern by reflected light and that of a pattern other than the uppermost-layer wiring pattern by the reflected light is larger than a predetermined value in the second linearly polarized light; and a selected wavelength light component guiding step of guiding a light component in the wavelength region selected by the selection step.

Therefore, the above-described means are taken in the wiring pattern detection method of the twenty-fifth aspect of the present invention, and accordingly the wavelength region in which the difference between the amount of the uppermost-layer wiring pattern by the reflected light and that of the pattern other than the uppermost-layer wiring pattern by the reflected light is larger than the predetermined value is selected in the second linearly polarized light, and an image constituted of the light component in the selected wavelength region can be picked up. Consequently, the image visualized into the uppermost-layer wiring pattern can be obtained.

According to a twenty-sixth aspect of the present invention, in the wiring pattern detection method of the twenty-fifth aspect of the present invention, the base film is formed of a polyimide resin, the wiring pattern is formed of copper, the selection step selects a wavelength region including 550 nm, and the image pickup step picks up the image by a CCD.

Therefore, the above-described means are taken in the wiring pattern detection method of the twenty-sixth aspect of the present invention, and accordingly the uppermost-layer wiring pattern concerning the work formed of polyimide resin and copper which are typical materials of the base film and wiring pattern can be detected with good precision.

According to a twenty-seventh aspect of the present invention, in the wiring pattern detection method of the nineteenth or twentieth aspects, the work is irradiated with elliptically polarized light instead of the circularly polarized light.

Therefore, when the above-described means are taken in the wiring pattern detection method of the twenty-seventh aspect of the present invention, the work can be irradiated with not only the circularly polarized light but also the elliptically polarized light.

According to a twenty-eighth aspect of the present invention, in the wiring pattern detection method of any one of the nineteenth to twenty-first aspects, the light source comprises a white light source.

Therefore, when the above-described means are taken in the wiring pattern detection method of the twenty-eighth aspect of the present invention, the white light source is usable as the light source without using any special light source.

According to a twenty-ninth aspect of the present invention, there is provided a wiring pattern inspection method comprising the steps of: collating an image picked up by the wiring pattern detection method according to any one of the nineteenth to twenty-first aspects with a predetermined satisfactory image to inspect whether or not the uppermost-layer wiring pattern is satisfactory.

Therefore, when the above-described means are taken in the wiring pattern inspection method of the twenty-ninth aspect of the present invention, it can be inspected with good precision whether or not the uppermost-layer wiring pattern is satisfactory.

BRIEF DESCRIPTION OF THE SEVERAL VIEWS OF THE DRAWING

FIG. 6A shows an image of an uppermost-layer wiring pattern picked-up by the inspection unit according to the present invention with respect to a multilayered wiring substrate for a semiconductor package, on which three layers of inner-layer wiring patterns exist via a polyimide insulating layer with respect to the uppermost-layer wiring pattern.

FIG. 6B shows an image picked-up by a conventional technique with respect to a multilayered wiring substrate for a semiconductor package, on which three layers of inner-layer wiring patterns exist via a polyimide insulating layer with respect to the uppermost-layer wiring pattern.

FIG. 13 is a constitution explanatory view showing one example of the inspection unit of the wiring is pattern inspection apparatus according to a third embodiment.

FIG. 14 is a constitution explanatory view showing one example of a parallel light guiding section in the inspection unit of the wiring pattern inspection apparatus according to the third embodiment.

FIG. 18A shows an image showing an example of the uppermost-layer wiring pattern picked up in the multilayered wiring substrate for the semiconductor package, on which one layer of the inner-layer wiring pattern exists.

FIG. 18B shows an image showing an example of the uppermost-layer wiring pattern picked up in the multilayered wiring substrate for the semiconductor package, on which three layers of the inner-layer wiring pattern exist.

FIG. 19A shows an image showing an example of the uppermost-layer wiring pattern picked up in the multilayered wiring substrate for the semiconductor package, on which one layer of the inner-layer wiring pattern exists.

FIG. 19B shows an image obtained by a binarizing process of the image of FIG. 19A.

DETAILED DESCRIPTION OF THE INVENTION

Embodiments of the present invention will be described hereinafter with reference to the drawings.

First Embodiment

A first embodiment of the present invention will be described with reference to FIGS. 1 to 9.

Figure 1:
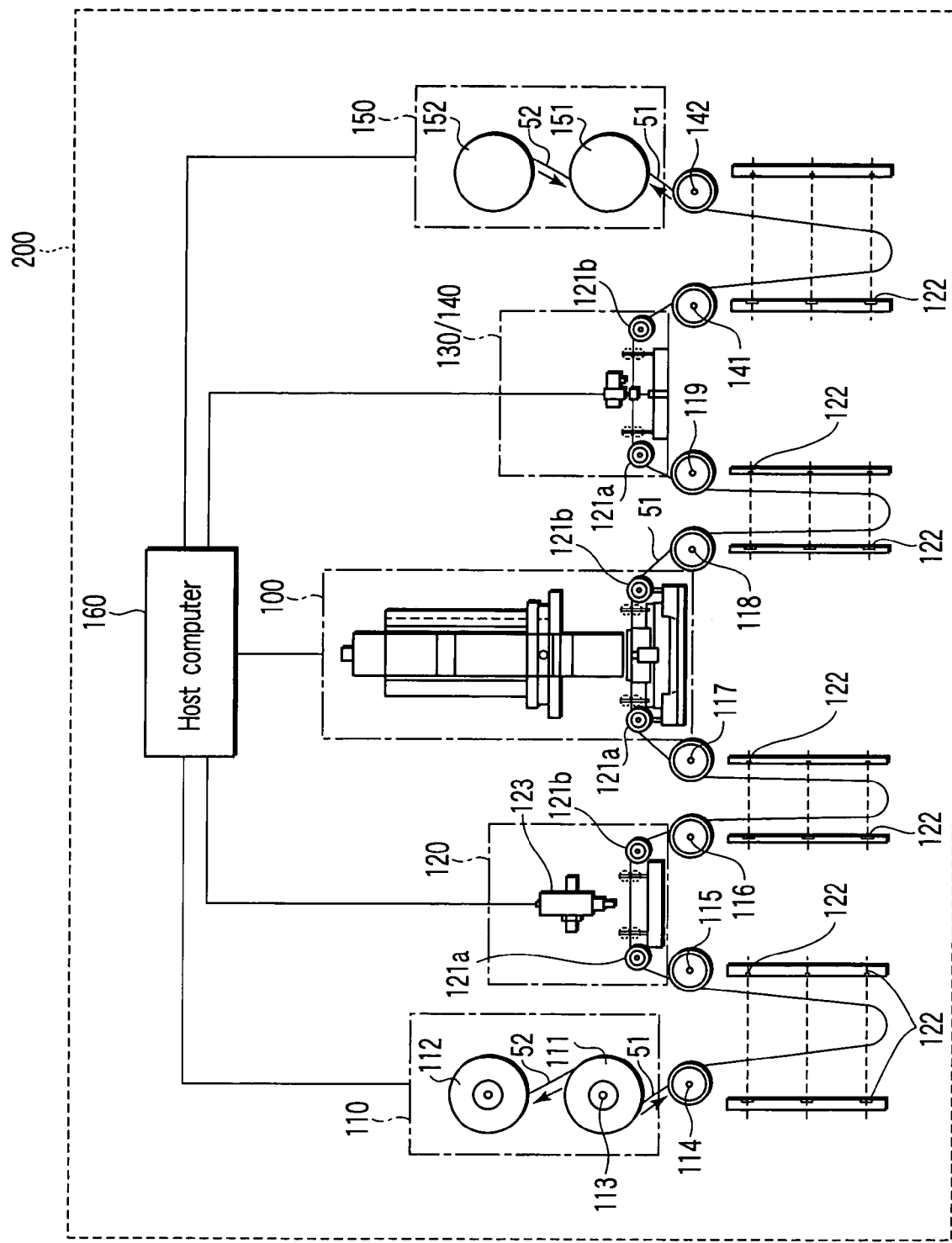
FIG. 1 is a constitution explanatory view showing one example of a wiring pattern inspection apparatus according to a first embodiment.

FIG. 1 is a constitution explanatory view showing one example of a wiring pattern inspection apparatus according to the present embodiment.

That is, a wiring pattern inspection apparatus 200 according to the present embodiment is a wiring pattern inspection apparatus which optically inspects an uppermost-layer wiring pattern of a work 51 comprising a multilayered wiring substrate for a semiconductor package, in which a wiring pattern is formed in a base film. The apparatus comprises an inspection unit 100, a work wind-out unit 110, a management code reader unit 120, a marking unit 130, a review/verify unit 140, a work wind-up unit 150, and a host computer 160.

In the work wind-out unit 110, a work reel 111 on which the work 51 is wound up is set in a lower stage, the work 51 is sent out by a roller 113 along a lower-stage work path, and a loosened amount is adjusted by upper/lower limit sensors 122 disposed in necessary/appropriate positions. A spacer tape 52 for protection, wound together with the work 51 on the work reel 111, is wound up by a spacer tape reel 112. State information of the work 51 is transmitted to the host computer 160.

Next, the work 51 is stabilized with high precision by tape conveying driving rollers 121a, 121b via guide rollers 114, 115. In this state, the work is conveyed to the management code reader unit 120, a management code (e.g., a mark in which work information is managed/coded, etc.) is read by a CCD camera 123, and the read management code is transmitted to the host computer 160.

Furthermore, the work 51 is stabilized with high precision by the tape conveying driving rollers 121a, 121b via guide rollers 116, 117. In this state, the work is conveyed to the inspection unit 100. The inspection unit 100 optically acquires the wiring pattern of an uppermost layer of the work 51. Moreover, wiring pattern data obtained by extracting characteristics of the acquired wiring pattern is compared with normal design wiring pattern data, and it is judged whether or not the wiring pattern is satisfactory. Moreover, a judgment result is transmitted to the host computer 160. Details of this inspection unit 100 will be described later.

The work 51 whose wiring pattern has been judged to be satisfactory or not by the inspection unit 100 is stabilized with high precision by the tape conveying driving rollers 121a, 121b via guide rollers 118, 119, and is conveyed to the marking unit 130 in this state. The marking unit 130 punches or marks otherwise the work 51 which is a defective article in such a manner as to identify the defective work 51. Moreover, this marking result is transmitted to the host computer 160. It is to be noted that examples of the marking method include print marking, taping, and another method in addition to the punching.

Next, in the review/verify unit 140, the wiring pattern is not only observed but also verified to confirm an excessive quality level. This confirmation result is transmitted to the host computer 160.

Furthermore, when a review function is provided with a length measurement function of the wiring pattern or an arbitrary component such as a defective component, a length measurement unit can be realized in addition to an inspector. Accordingly, regular information of a pattern width of one reel can be grasped, and this contributes to immediate feedback into steps.

Next, the work 51 is conveyed to the work wind-up unit 150 via guide rollers 141, 142. Moreover, the work is wound up together with the spacer tape 52 for the protection supplied from a spacer tape reel 152 in a work reel 151. State information of the work 51 in the work wind-up unit 150 is transmitted to the host computer 160.

The wiring pattern inspection apparatus 200 constituted in this manner has a unit constitution as a base. For example, addition/removal of a unit can be easily performed such as addition of the inspection unit 100 in order to raise a processing speed, and a structure or a constitution is achieved in consideration of use in a clean environment. The work conveyance or another constitution is not limited to the above-described mode. For example, the constitution is embodied by vertical conveyance, not transverse conveyance, both the work wind-out unit 110 and the work wind-up unit 150 are disposed on the same side, or another arrangement is also possible.

Details of the inspection unit 100 will be described hereinafter.

Figure 2:
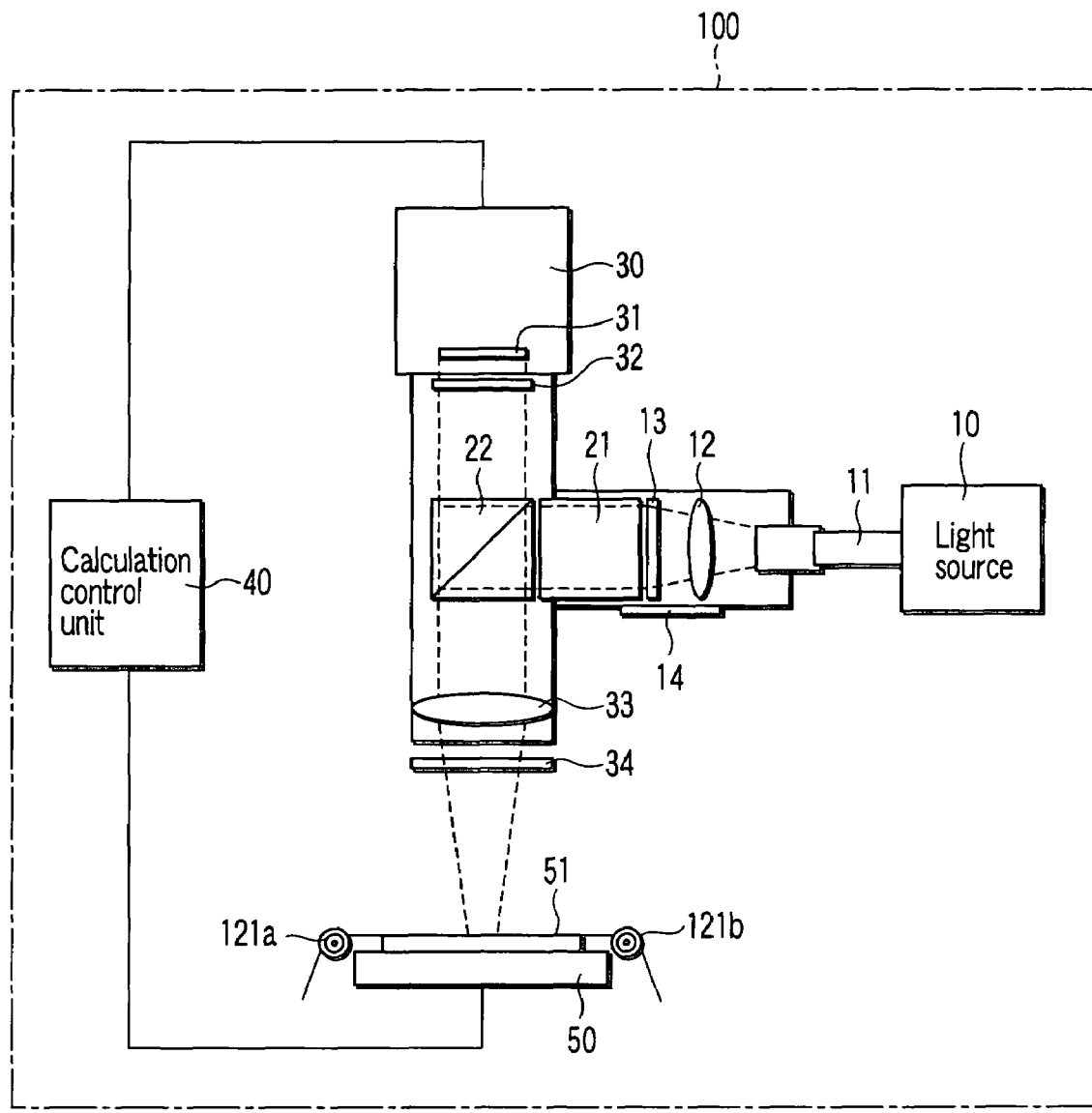
FIG. 2 is a constitution explanatory view showing one example of an inspection unit in the wiring pattern inspection apparatus according to the first embodiment.

As shown in FIG. 2, the inspection unit 100 comprises: a light source 10; a light guide 11; a condenser lens 12; a hot-wire cut filter 13; a heat radiation mechanism 14; a polarized beam splitter 21; a polarized beam splitter 22; a sensor camera 30; a CCD device 31; a bandpass filter 32; an image forming lens 33; a polarization filter 34 (polarization plate); a calculation control unit 40; and a work fixing/driving mechanism 50. It is to be noted that each of the condenser lens 12 and the image forming lens 33 is not limited to a single lens, and may be a lens group comprising a plurality of lenses.

As the light source 10, high-luminance illumination which emits light over a whole visible range is preferable such as a white light source and metal halide lamp. A sufficient quantity of light is required in order that the image should be picked up by the CCD device 31 with high resolution as described later. Therefore, as the light source 10, for example, a metal halide lamp having a power rating of 250 W is changed to that of 350 W. As the light guide 11, a spot type capable of combining the light from a plurality of light sources 10 to emit an output from one end, or a rod lens is preferable. Additionally, when the number of light sources 10 for use is increased, a bundle diameter of the light guide 11 or an outer shape needs to be enlarged, and therefore the condenser lens 12 requires to be devised. A heat measure by infrared light included in the light from the light source 10 needs to be also taken.

When the light is emitted from the light source 10, the light enters the polarized beam splitter 21 via the light guide 11, condenser lens 12, and hot-wire cut filter 13. The hot-wire cut filter 13 interrupts light on a long wavelength side (e.g., wavelength of 700 nm or more), and allows another light to enter the polarized beam splitter 21.

The light emitted from the light source 10 is so-called random light having light components of many directions. It is to be noted that in this case, a "light guiding direction" is defined as a horizontal direction from right to left in FIG. 2. The polarized beam splitter 21 extracts linearly polarized light (front/back direction in the figure is an electric-field vector direction) from this random light. Therefore, an appropriate polarized beam splitter 21 needs to be selected sufficiently considering an applied wavelength region, quenching ratio, polarization ratio, outer shape size capable of irradiating a whole work view field or forming an image and the like. The polarized beam splitter 21 obtains the linearly polarized light in this manner, but 100% linearly polarized light is not necessarily extracted, and additionally a slight amount of a light component whose electric-field vector is other than the front/back direction in the figure is included.

It is to be noted that the polarized beam splitter 21 and hot-wire cut filter 13 are at high temperature by the light of the light source 10. Since there is a fear of breakage, or deterioration of an optical member itself, the heat radiation mechanism 14 is disposed. The heat radiation mechanism 14 spouts air from the outside to thereby cool the polarized beam splitter 21 and the hot-wire cut filter 13. For example, when one 250 W metal halide lamp is used as the light source 10, the hot-wire cut filter 13 is at high temperature of about 75° C., but an experiment example is obtained indicating that air can be spouted by the heat radiation mechanism 14 to thereby reduce the temperature to about 50° C.

The polarized beam splitter 21 guides the extracted linearly polarized light to the polarized beam splitter 22. At this time, the light component which is not guided into the polarized beam splitter 22 escapes to a lens tube side wall in the polarized beam splitter 21, and therefore a heat measure needs to be applied in a side wall portion. A gap between the polarized beam splitters 21 and 22 is set to be as small as possible in order to minimize light propagation loss.

A slight amount of light whose electric-field vector is other than the front/back direction is also included in the light guided from the polarized beam splitter 21, and is therefore removed by the polarized beam splitter 22. The light is further guided downwards. Moreover, the image forming lens 33 and the polarization filter 34 convert this linearly polarized light into light of an angle component having a rotation angle of 40 to 50°, and the work 51 fixed by the work fixing/driving mechanism 50 is irradiated. The work 51 is irradiated with a light component obtained by vector-resolving the incident linearly polarized light in accordance with the rotation angle. It is to be noted that in FIG. 2, the image forming lens 33 is disposed between the polarized beam splitter 22 and the polarization filter 34, but the polarization filter 34 may be disposed between the polarized beam splitter 22 and the image forming lens 33. A rotation mechanism may be appropriately disposed in such a manner that the polarization filter 34 is capable of easily selecting light including only a certain angle component.

The light component with which the work 51 is irradiated is reflected by the work 51, and the light component obtained by vector-resolving this reflected light in accordance with the rotation angle of the polarization filter 34 enters the polarized beam splitter 22 via the polarization filter 34 and image forming lens 33. At this time, in the polarized beam splitter 22, the linearly polarized light whose electric-field vector direction is in a light guiding direction is extracted, and this linearly polarized light enters the bandpass filter 32.

The bandpass filter 32 extracts a wavelength region in which a difference between a reflected light quantity of the uppermost-layer wiring pattern and a quantity from the polarized beam splitter 22 by the reflected light of a polyimide insulating layer portion is maximized, and only light of the extracted wavelength region enters the CCD device 31 in the sensor camera 30.

Figure 3:
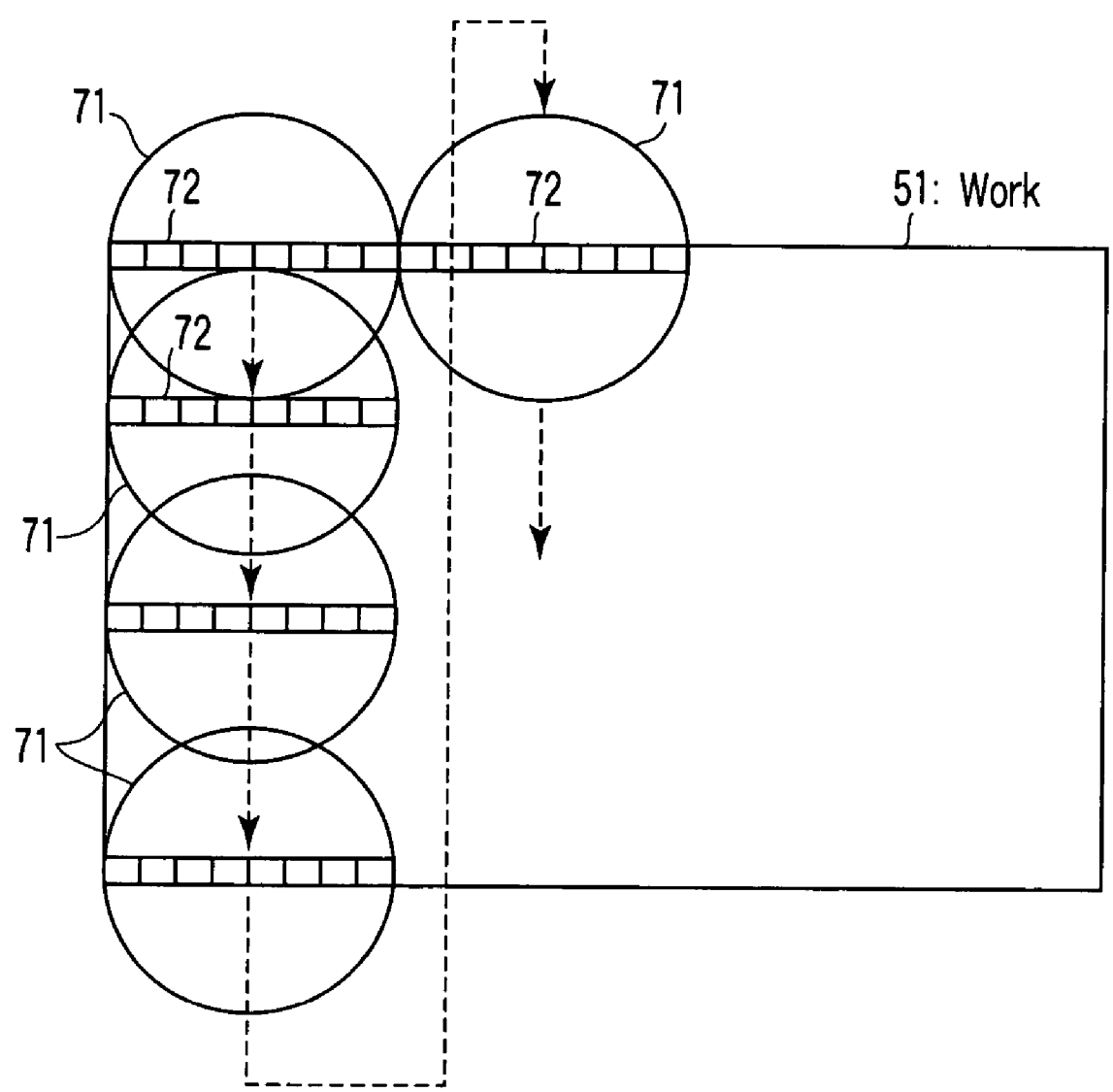
FIG. 3 is a schematic diagram showing a relation between an irradiation region and a linear region in a work.

In the present embodiment, a line sensor technique is applied to the sensor camera 30. FIG. 3 is a schematic diagram showing the line sensor technique. That is, in the sensor camera 30, only light corresponding to a linear region predetermined as a specification of the CCD device 31 is imaged by the CCD device 31 among the light which has entered the CCD device 31 by the bandpass filter 32. In FIG. 3, circular irradiation regions 71 indicate regions of the work 51 irradiated with the light component. Each of the above-described linear regions 72 is positioned in such a manner as to pass through a center of each irradiation region 71. The CCD device 31 picks up an image in a state in which an optical head of the sensor camera 30 or the work fixing/driving mechanism 50 is adjusted in a required take-in direction, when flatness of the work 51 is secured in a focal depth of the image forming lens 33 by the work fixing/driving mechanism 50 for the work 51, and the irradiation region 71 as a part of the work 51 is irradiated with the light component. Accordingly, the sensor camera 30 images the light in the linear region 72 corresponding to the irradiation region 71.

When the light in the certain linear region 72 is imaged in this manner, the work fixing/driving mechanism 50 is driven, the work 51 is moved by a micro amount, for example, as shown by an arrow in FIG. 3, and accordingly the irradiation region 71 is moved. Moreover, the light in the linear region 72 corresponding to the irradiation region 71 is similarly imaged. The micro-amount movement and the imaging of the work 51 are continuously performed until the linear regions 72 cover the whole surface of the work 51. Moreover, when the respective imaged linear regions 72 are superimposed upon one another to thereby obtain imaging information over the whole surface of the work 51, a wiring pattern image is obtained in which uppermost-layer wiring pattern information is acquired.

Since the wiring pattern of the work 51 constituting an object is 10 μm at minimum, and fine, the sensor camera 30 and the image forming lens 33 optically designed in such a manner that the picked-up image has high resolution are used. The resolution is preferably about 1 to 2 μm by which pattern edge information is sufficiently clearly obtained, but an aim of this resolution setting is about ⅕ to ¹⁄₁₀ of a pattern width which is an object. Since an imaging view field also changes with the number of devices and resolution with respect to the CCD device 31 of the sensor camera 30 for use, the resolution needs to be sufficiently studied. For example, the imaging view field is 8 mm in a case where a resolution of 1 μm is realized by the CCD device 31 having 8000 pixels.

Moreover, assuming that a size of the CCD device 31 is 7 μm, an optical magnification of seven times is naturally required. A resolving power obtained at this time is 721 p (line pair)/mm on an object side. To realize a resolution of 1 μm, the image cannot be picked up with equal brightness unless there is a quantity of light of about 50 times in accordance with an area ratio with respect to the resolution of 7 µm. A logical sum having various conditions is required in an optical system.

Moreover, in the bandpass filter 32, for example, as in a dichroic green filter, a filter having a wavelength region in which a difference between the reflected light quantity of the uppermost-layer wiring pattern and that of the polyimide insulating layer portion is maximized, and high transmittance is used. Specifically, when a wavelength of 550 nm which is a green component is noted, reflection spectral sensitivity of copper is 3% whereas that of the polyimide layer is 0.1%, and 30 times the light is reflected as obtained from experiment values.

That is, since intensity of the light component reflected by the work 51 depends on copper and polyimide, and copper has stronger reflection intensity, an uppermost-layer copper pattern portion can be brightly imaged. When the work 51 is irradiated, the polarization ratio is increased, the wiring pattern and polyimide insulating layer are irradiated, and accordingly the image of the uppermost-layer wiring pattern is more clearly picked up.

Wiring pattern data of the wiring pattern image in which the uppermost-layer wiring pattern information is acquired in this manner is output to the calculation control unit 40 comprising a personal computer, keyboard, mouse, display and the like (not shown), and displayed in the display. In the calculation control unit 40, various calculation, recognition, and comparison processes are performed using output wiring pattern data and normal design wiring pattern data, and it is judged whether or not the wiring pattern is satisfactory. The calculation control unit 40 also has a role of a user interface which controls the work fixing/driving mechanism 50 or the like.

Next, an operation of the inspection unit of the wiring pattern inspection apparatus according to the present embodiment constituted as described above will be described.

That is, in the inspection unit 100, when the light is emitted from the light source 10, the light is guided to the hot-wire cut filter 13 via the light guide 11 and condenser lens 12. Moreover, the light (e.g., a wavelength of 700 nm or more) on the long wavelength side is interrupted by the hot-wire cut filter 13, and another light is guided into the polarized beam splitter 21.

The light emitted from the light source 10 is random light, and the linearly polarized light (front/back direction in the figure is a direction of an electric-field vector) is extracted from the random light in the polarized beam splitter 21, and guided to the polarized beam splitter 22. It is to be noted that 100% of the linearly polarized light (front/back direction in the figure is the direction of the electric-field vector) is not necessarily extracted by the polarized beam splitter 21, and a slight amount of a light component of the electric-field vector other than the front/back direction in the figure is included.

It is to be noted that the polarized beam splitter 21 and the hot-wire cut filter 13 are at high temperature by the light of the light source 10, and are cooled by the air spouted by the heat radiation mechanism 14.

Little light including the electric-field vector other than the front/back direction is included in the light guided from the polarized beam splitter 21, and is therefore removed by the polarized beam splitter 22. Moreover, the light is guided toward the image forming lens 33 and the polarization filter 34. Furthermore, the work 51 in which a predetermined deflected component obtained via the polarization filter 34 having the predetermined angle is fixed by the work fixing/driving mechanism 50 is irradiated with the linearly polarized light extracted by the polarized beam splitter 22.

The light component with which the work 51 is irradiated is reflected by the work 51, and the reflected light passes through the polarization filter 34, and is converted into linearly polarized light (right/left direction in the figure is an electric-field direction) crossing the electric-field vector direction of the linearly polarized light at right angles.

Thereafter, the light is formed into parallel light by the image forming lens 33, and the linearly polarized light whose electric-field vector direction is the right/left direction in the figure is extracted by the polarized beam splitter 22, and is thereafter guided to the bandpass filter 32.

In the bandpass filter 32, the wavelength region in which the difference between the amount of the uppermost-layer wiring pattern by the reflected light and the amount of the polyimide insulating layer portion by the reflected light is maximized is extracted, and the only light of the wavelength region is transmitted into the CCD device 31 in the sensor camera 30. Specifically, in the wavelength of 550 nm which is the green component, the reflection spectral sensitivity of the polyimide layer is 0.1%, whereas that of copper is 3%, and 30 times reflection is obtained from the experiment value. When the light extracted in this manner is imaged by the CCD device 31, the image of the wiring pattern whose uppermost-layer wiring pattern information has been visualized is obtained. That is, since the intensity of the light component reflected by the work 51 depends on copper and polyimide, and copper has stronger reflection intensity, the uppermost-layer copper pattern portion is brightly imaged. When the work 51 is irradiated, the polarization ratio is increased, the wiring pattern and polyimide insulating layer are irradiated, and accordingly the clearer image of the uppermost-layer wiring pattern is picked up.

Figure 4D:
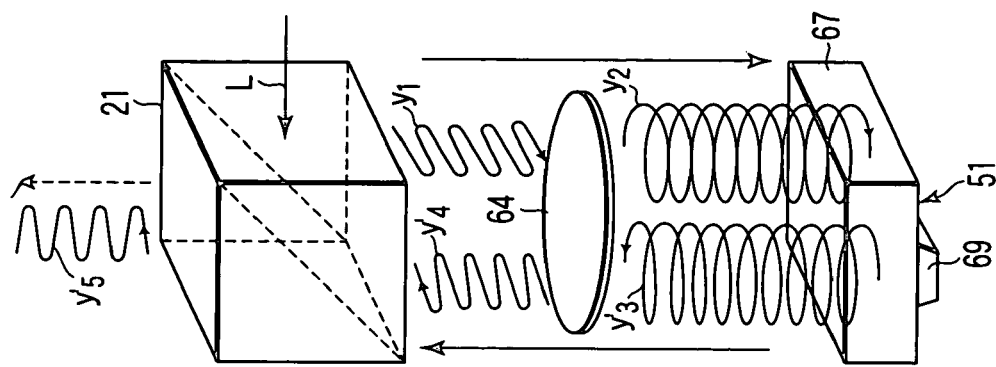
FIG. 4D is a schematic diagram showing a principle for obtaining a wiring pattern image in which uppermost-layer wiring pattern information is visualized.
Figure 4C:
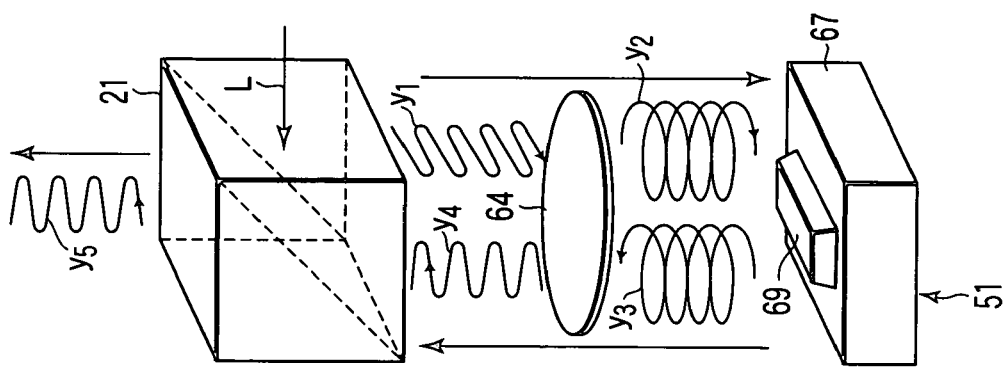
FIG. 4C is a schematic diagram showing a principle for obtaining a wiring pattern image in which uppermost-layer wiring pattern information is visualized.
Figure 4B:
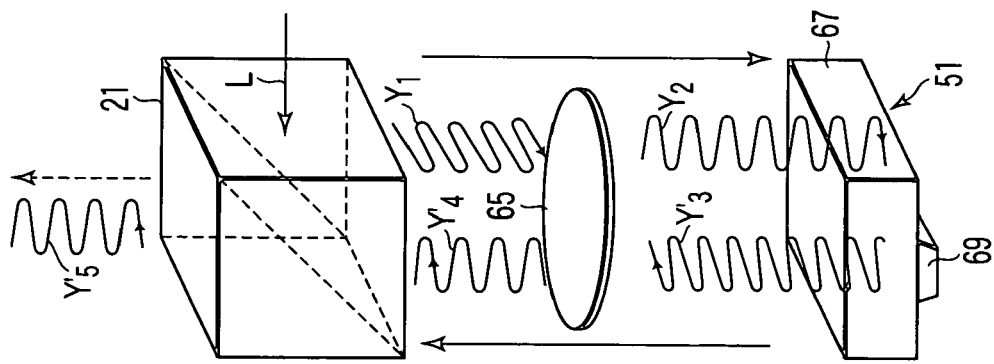
FIG. 4B is a schematic diagram showing a principle for obtaining a wiring pattern image in which uppermost-layer wiring pattern information is visualized.
Figure 4A:
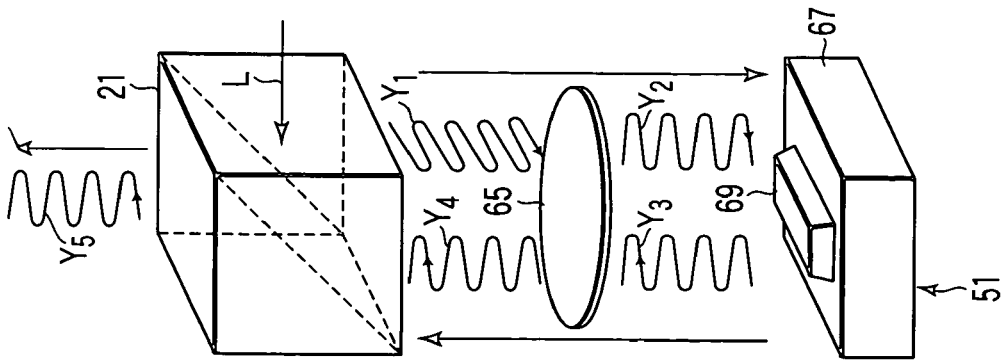
FIG. 4A is a schematic diagram showing a principle for obtaining a wiring pattern image in which uppermost-layer wiring pattern information is visualized.
Figure 5A:
FIG. 5A shows a picked-up image of the wiring pattern in a case where a rotation angle of a polarization filter is set to 0° in the inspection unit shown in FIG. 2.
Figure 5B:
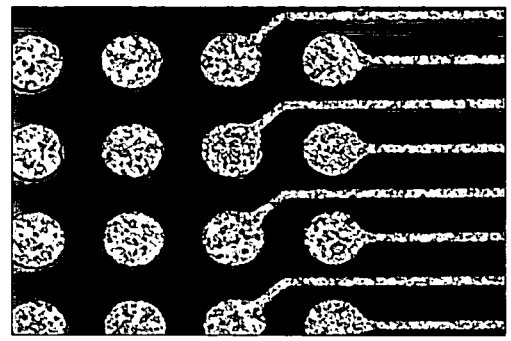
FIG. 5B shows a picked-up image of the wiring pattern in a case where the rotation angle of the polarization filter is set to 10° in the inspection unit shown in FIG. 2.
Figure 5C:
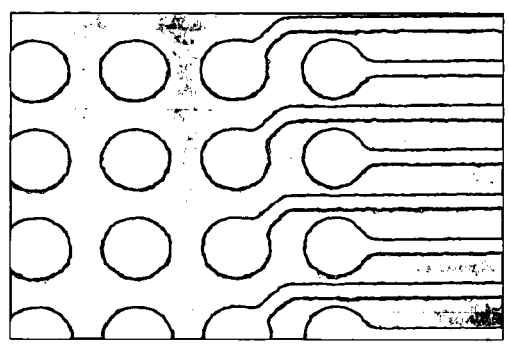
FIG. 5C shows a picked-up image of the wiring pattern in a case where the rotation angle of the polarization filter is set to 45° in the inspection unit shown in FIG. 2.
Figure 5D:
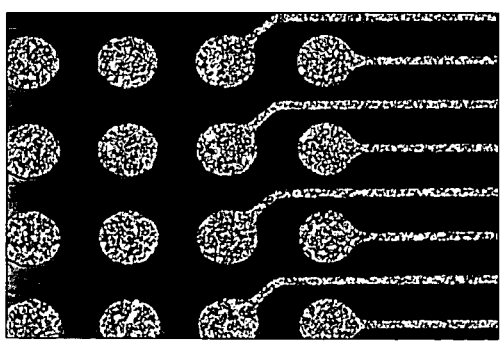
FIG. 5D shows a picked-up image of the wiring pattern in a case where the rotation angle of the polarization filter is set to 80° in the inspection unit shown in FIG. 2.
Figure 5E:
FIG. 5E shows a picked-up image of the wiring pattern in a case where the rotation angle of the polarization filter is set to 90° in the inspection unit shown in FIG. 2.

This principle will be described with reference to FIGS. 4A and 4B. That is, linearly polarized light $Y_1$ whose electric-field vector direction is in the front/back direction in FIG. 2 is extracted, and guided from the light guided by the light guide 11 which guides light L from the light source 10 in parallel via polarization plates or polarized beam splitters combined in many stages. FIGS. 4A and 4B show an example in which the linearly polarized light $Y_1$ is extracted and guided by the polarized beam splitter 21.

Moreover, the light is guided to a polarization plate 65 whose optical axis is adjusted at an arbitrary angle with respect to the linearly polarized light $Y_1$. A polarization plate optimum angle (optimum angle formed by the front/back direction of FIG. 2 and a transmission axis of the polarization plate 65) is 45° with respect to the linearly polarized light $Y_1$ at this time. Therefore, an effect under 45° conditions will be described hereinafter.

Additionally, the light transmitted through the polarization plate 65 whose optical axis has been adjusted at 45° constitutes a component obtained by vector-resolving the incident linearly polarized light $Y_1$ by $1/\sqrt{2}$ time. The work 51 in which a wiring pattern 69 is disposed on a base 67 of a polyimide film insulating material or the like is irradiated with this $1/\sqrt{2}$ linearly polarized light $Y_2$.

As shown in FIG. 4A, when the wiring pattern 69 of copper or the like is irradiated with this $1/\sqrt{2}$ linearly polarized light $Y_2$, the incident $1/\sqrt{2}$ linearly polarized light $Y_2$ is simply reflected by the surface of the wiring pattern 69 of copper or the like formed by copper plating means or the like. Moreover, reflected $1/\sqrt{2}$ linearly polarized light $Y_3$ passes through the polarization plate 65 again. At this time, as to light $Y_4$ passing through the polarized beam splitter 21, a component obtained by vector-resolving the $1/\sqrt{2}$ linearly polarized light $Y_3$ reflected by the work 51 further into $1/\sqrt{2}$ passes above the polarized beam splitter 21. This light component $Y_5$ is simply received as a component having information of the wiring pattern 69 of the uppermost layer by the CCD device 31.

Similarly, as shown in FIG. 4B, a transparent base film 67 of a polyimide film insulating material or the like is irradiated with this $1/\sqrt{2}$ linearly polarized light $Y_2$. It is seen that this transparent base film 67 has anisotropy in a material property. That is, it is supposed that the $1/\sqrt{2}$ linearly polarized light $Y_2$ incident upon the transparent base film 67 is reflected as polarized light or random light to which an angle change has been added by the surface of the film. Since reflected light $Y_3'$ deviates from a polarization plate angle of 45°, the light has a light quantity to such an extent that light is hardly received as compared with a relative light quantity of 0.5 received by the CCD device 31 at 45°. That is, a light quantity difference received by the CCD device 31 is made between a case where the wiring pattern 69 of copper or the like is irradiated and a case where the transparent base film 67 of the polyimide insulating portion or the like is irradiated. An information component corresponding to the transparent base film 67 of the polyimide film insulating material or the like is supposed to be hardly guided to the CCD device 31.

Therefore, when information is well extracted in accordance with a material characteristic forming the semiconductor package in this manner, and received by the CCD device 31, it is possible to pick up the uppermost-layer wiring pattern information as an image having high contrast while the inner-layer wiring pattern is not reflected.

Moreover, FIG. 6A shows an image showing one example of an uppermost-layer wiring pattern picked-up by the sensor camera 30, after acquiring the uppermost-layer wiring pattern information by the inspection unit 100, with respect to the multilayered wiring substrate for the semiconductor package, on which three layers of inner-layer wiring patterns exist via a polyimide insulating layer with respect to the uppermost-layer wiring pattern. On the other hand, FIG. 6B shows an image picked-up usually by a camera with respect to the same uppermost-layer wiring pattern.

It can be confirmed from FIGS. 6A and 6B that the wiring pattern information of the uppermost layer is optically acquired by the inspection unit 100, and accordingly the uppermost-layer wiring pattern can be clearly extracted even in a case where there are three layer of inner-layer wiring patterns. It is possible to extract the only uppermost-layer wiring pattern without depending on the number of added inner layers regardless of presence of the wiring pattern.

On the other hand, as shown in FIG. 6B, the wiring patterns of all layers are reflected in the usual imaging by the camera. Furthermore, since the uppermost-layer wiring pattern has the same degree of brightness as that of the inner-layer wiring pattern, the patterns cannot be separated even when subjected, for example, to a binarizing process. Especially, influence is remarkable in a portion in which the uppermost-layer wiring pattern intersects with the inner-layer wiring pattern, and the pattern existing on the upper side is not easily identified.

Figure 7A:
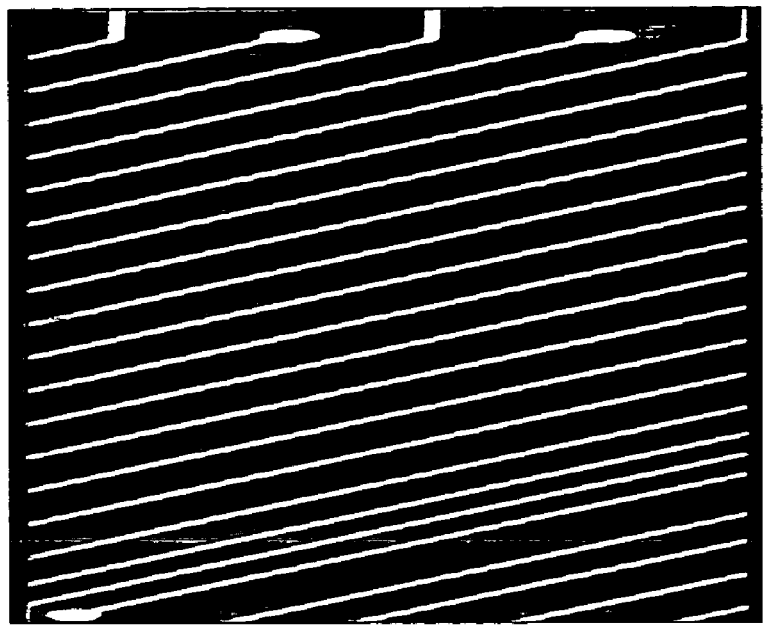
FIG. 7A shows an image of an uppermost-layer wiring pattern obtained by the inspection unit according to the present invention with respect to a multilayered wiring substrate for a semiconductor package, on which one layer of inner-layer wiring pattern exists via a polyimide insulating layer with respect to the uppermost-layer wiring pattern.
Figure 8:
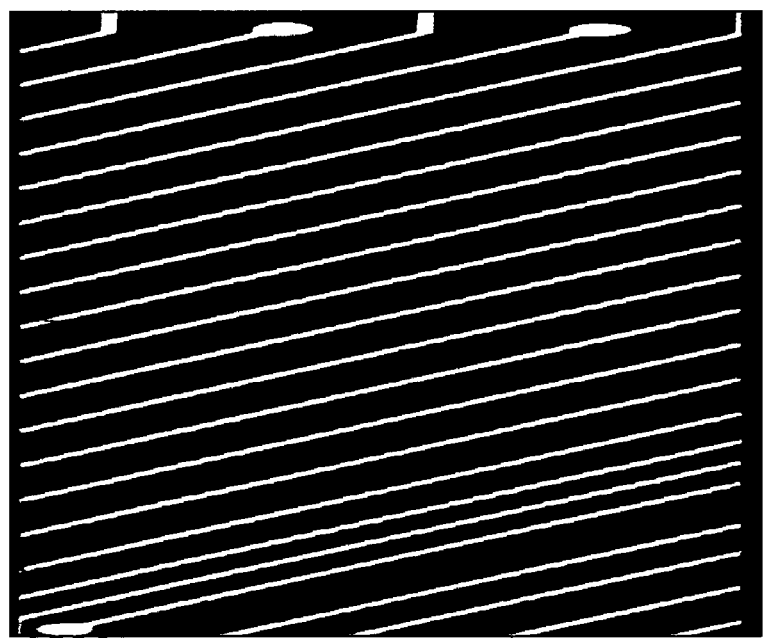
FIG. 8 shows an image obtained by a binarizing process of the image shown in FIG. 15.
Figure 7B:
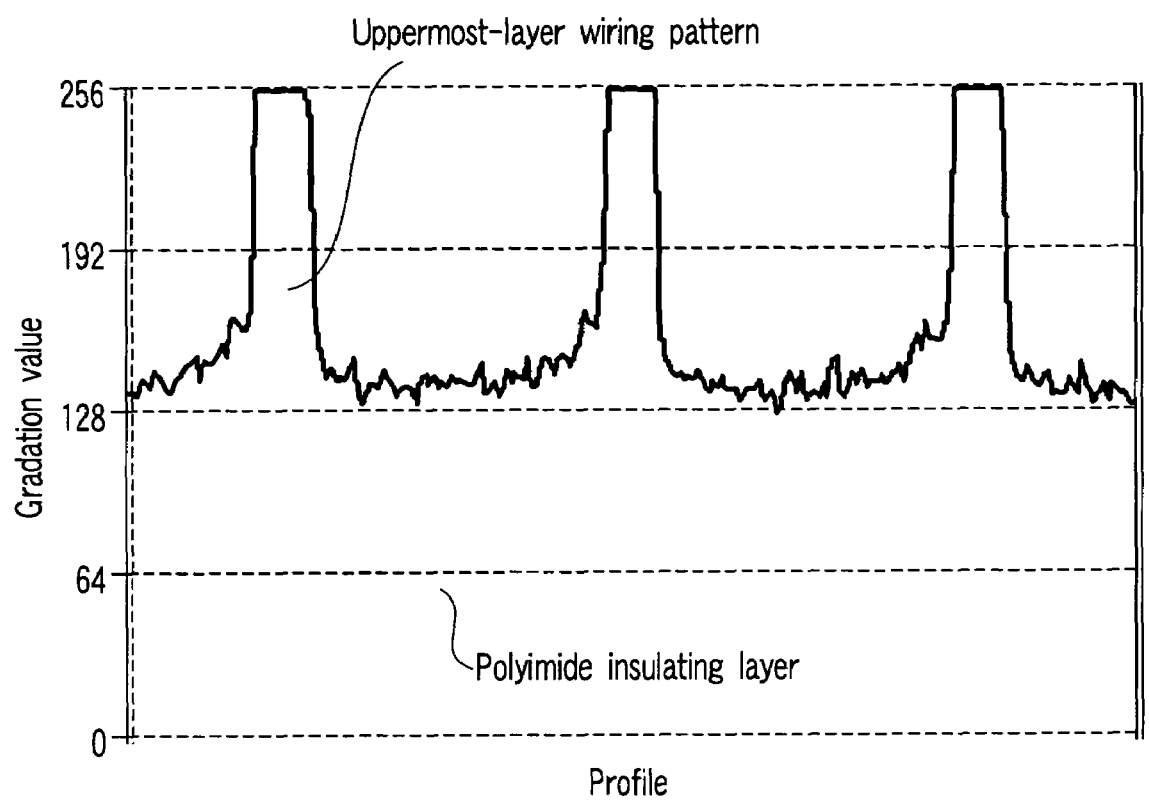
FIG. 7B shows a line profile corresponding to the image of FIG. 15.

Moreover, FIG. 7A shows an image showing another example of the uppermost-layer wiring pattern picked up by the CCD device 31, after acquiring the uppermost-layer wiring pattern information by the inspection unit 100, with respect to the multilayered wiring substrate for the semiconductor package, on which one layer of inner-layer wiring pattern exists via a polyimide insulating layer with respect to the uppermost-layer wiring pattern. FIG. 7B shows a line profile corresponding to the wiring pattern portion shown in the image of FIG. 7A. FIG. 8 shows an image obtained by a binarizing process performed with respect to the image shown in FIG. 7A.

As apparent from FIG. 8, it is seen that the uppermost-layer wiring pattern portion is bright, and the inner-layer pattern and polyimide insulating layer portion are imaged to be dark. Thus, the image picked up by the inspection unit 100 can be classified further into the uppermost-layer wiring pattern and inner-layer wiring pattern without being influenced by the inner-layer wiring pattern by simple image processing referred to as a binarizing process. Moreover, CAD data (pattern design information) or satisfactory work (work in which the wiring pattern is correctly formed) is set as a reference master image in advance, and a portion having a difference can be judged as a defect by comparison with the binarized image, characteristic extraction method or the like.

Moreover, an image optimum for pattern inspection indicates a state in which a pattern edge is clear and there is not any influence of surface irregularity. A contrast difference between the wiring pattern portion and the polyimide insulating layer portion has to be clearly segmented in order that the pattern edge should be clear. Therefore, a light quantity with which the work is irradiated has to be large, and the work has to be bright in order to eliminate the influence of the wiring pattern surface irregularity.

Figure 9:
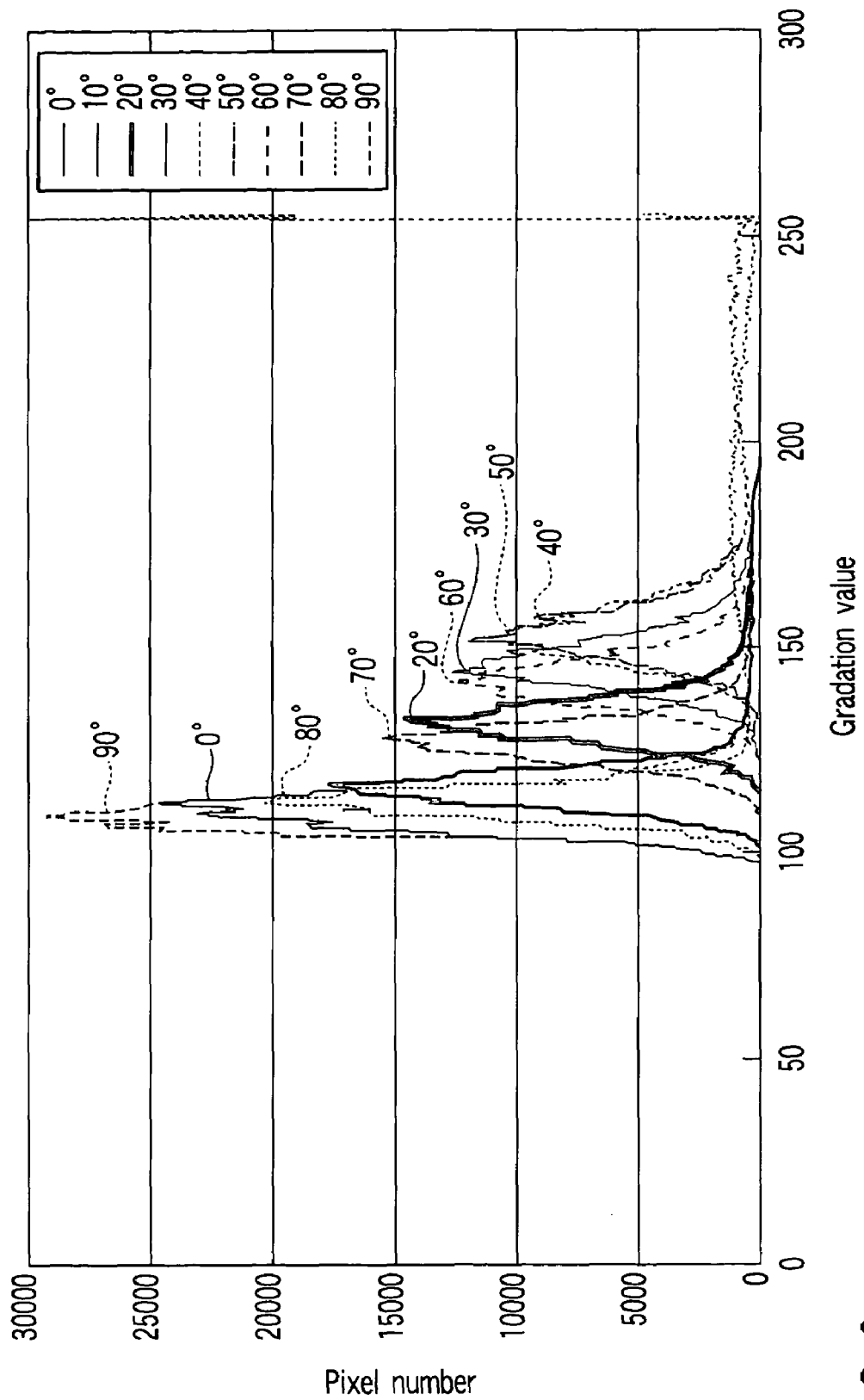
FIG. 9 shows one example of histogram of a wiring pattern image in a case where a rotation angle of a polarization filter of the inspection unit is changed in the wiring pattern inspection apparatus according to the first embodiment.

FIG. 9 shows one example of histogram of the wiring pattern image in a case where a transmission axis of the polarization filter 34 is changed by a predetermined angle in a direction of electric-field vector of the first linearly polarized light, the abscissa indicates gradation values, and the ordinate indicates the number of pixels. A condition on which the histogram shifts most on a high gradation side is a rotation angle of 40° to 50°, and it can be confirmed that an area of a peak of the histogram also decreases at this rotation angle as compared with another rotation angle.

A polyimide insulating layer portion or a wiring pattern portion is included in a gradation range of this peak at another rotation angle. However, the wiring pattern portion has a maximum gradation when approaching the optimum angle. Therefore, the wiring pattern portion is separated from the area of the peak, and the peak area decreases. It can be similarly confirmed also from the image picked up at each rotation angle that an optimum condition on which the wiring pattern portion is clear and a contrast difference between the wiring pattern portion and the polyimide insulating layer portion is large is a rotation angle in a range of 40° to 50°.

In another rotation angle, the gradation value of the wiring pattern portion decreases, and accordingly the contrast difference between the wiring pattern portion and the polyimide insulating layer portion decreases. Consequently, the gradation value of the wiring pattern portion drops, and the influence of the irregularity of the wiring pattern surface also remarkably appears. Therefore, the image is not suitable as a pattern inspection image. The images of the respective angle components are shown in FIGS. 5A to 5E.

As described above, in the wiring pattern inspection apparatus according to the present embodiment, the influence of the inner-layer wiring pattern can be optically removed in the multilayered wiring substrate for the semiconductor package by the above-described function. As a result, a fine image of the uppermost-layer wiring pattern can be picked up.

Furthermore, when this image is compared with reference data or reference image, it is possible to perform the inspection of the wiring pattern automatically with high reliability.

Moreover, when the line sensor technique is applied to the sensor camera 30, the image can be picked up in a short time as compared with a case where an image is obtained by point scanning applied, for example, as in Jpn. Pat. No. 2962565. Therefore, the technique is advantageously even for the uppermost-layer wiring pattern having a large area.

Furthermore, since the wiring pattern can be inspected based on the image picked up by the sensor camera 30, it is not necessary to doubly dispose a detection system as in Jpn. Pat. No. 2962565, and the constitution can be simplified. Additionally, since data processing of a detected value also decreases, it is possible to reduce a load of the calculation control unit 40.

Second Embodiment

A second embodiment of the present invention will be described with reference to FIGS. 2 and 10 to 12.

A wiring pattern inspection apparatus according to the present embodiment relates to improvement of a polarized beam splitter 21 in an inspection unit 100 of a wiring pattern inspection apparatus according to the first embodiment. Therefore, here, the only polarized beam splitter 21 will be described.

That is, in the first embodiment of FIG. 2, the polarized beam splitter 21 extracts linearly polarized light (front/back direction in the figure is an electric-field vector direction) from random light emitted from the light source 10. However, a light component in which a vertical direction in FIG. 2 is an electric-field vector direction escapes to the side face from the polarized beam splitter 21 at an extraction time, and therefore the side face is at high temperature.

Therefore, when this light component can be recovered, converted into the light component whose electric-field vector direction is a front/back direction in the figure, and guided into the polarized beam splitter 22, a light quantity further increases, and it is possible to enlarge a contrast difference between a wiring pattern portion and a polyimide insulating layer portion.

Figure 10:
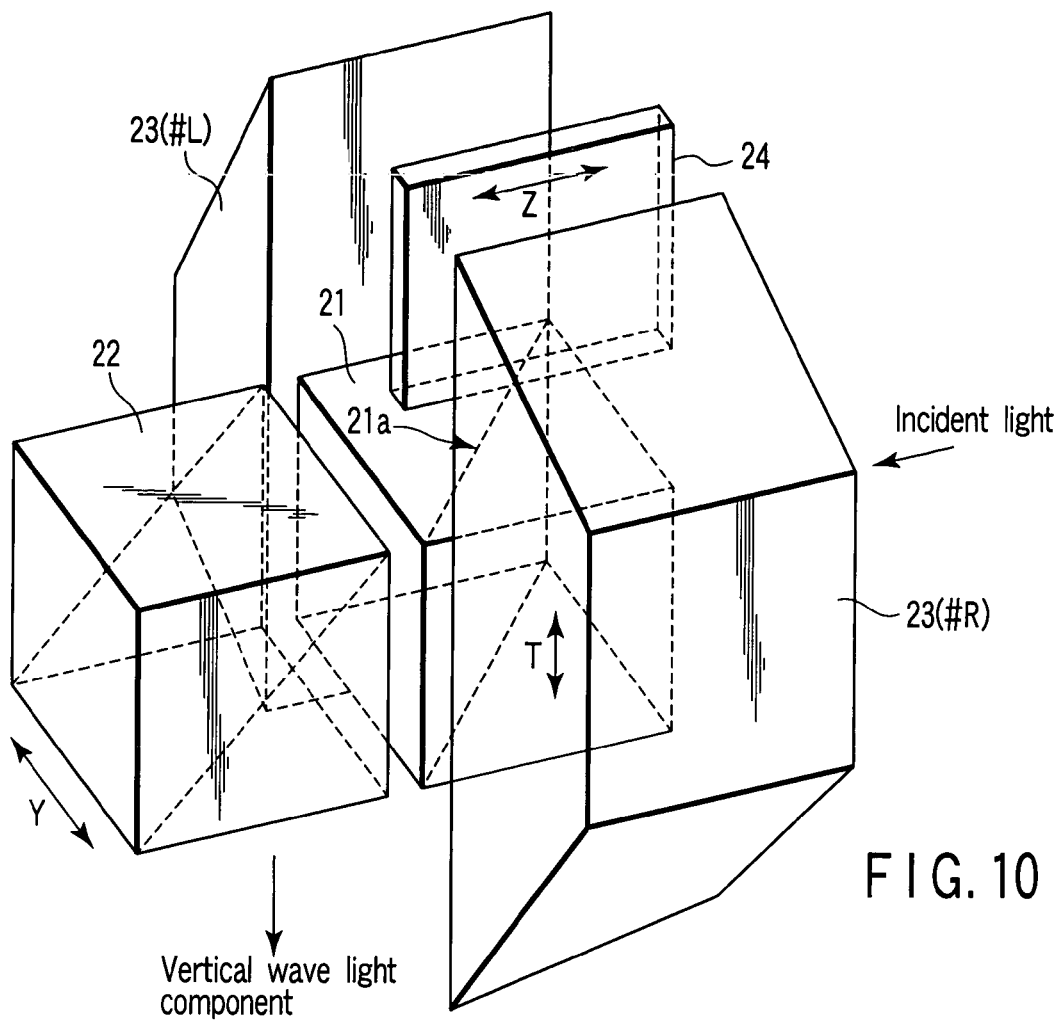
FIG. 10 is a perspective view showing a whole constitution example of a polarized beam splitter in the wiring pattern inspection apparatus according to a second embodiment.

FIG. 10 is a perspective view showing one example of a whole constitution of the polarized beam splitter 21 for realizing this embodiment.

That is, as shown in FIG. 10, the polarized beam splitter 21 in the present embodiment comprises a polarization film 21a, and further a tab prism 23 (#R) and a tab prism 23 (#L) are disposed on opposite side faces. A half-wavelength plate 24 is disposed above.

That is, when random light is introduced into the polarized beam splitter 21 from the light source 10, a light component Y whose electric-field vector direction is a front/back direction in the figure is extracted from the random light by the polarized beam splitter 21, and guided into the polarized beam splitter 22. On the other hand, at this extraction time, a light component T whose electric-field vector direction is a vertical direction in FIG. 2 escapes from the side face, and is introduced into the tab prism 23 (#R). The tab prism 23 (#R) takes in the light component T which has escaped and whose electric-field vector direction is the vertical direction in FIG. 2, and guides the component into the half-wavelength plate 24. The half-wavelength plate 24 converts the light component T which is introduced from the tab prism 23 (#R) and whose vertical direction in FIG. 2 is the electric-field vector direction by a half-wavelength. That is, the component is converted into a light component Z whose electric-field vector direction is a right/left direction in the figure, and guided into the tab prism 23 (#L). The tab prism 23 (#L) guides the light component Z whose electric-field vector direction guided from the half-wavelength plate 24 is the right/left direction in the figure from the side face into a main body of the polarized beam splitter 21. The polarization film 21a reflects the light component Z whose electric-field vector direction guided in this manner is a right/left direction in the figure, accordingly converts the component into a light component Y whose electric-field vector direction is a front/back direction in the figure, and guides the component out to the polarized beam splitter 22.

Figure 11:
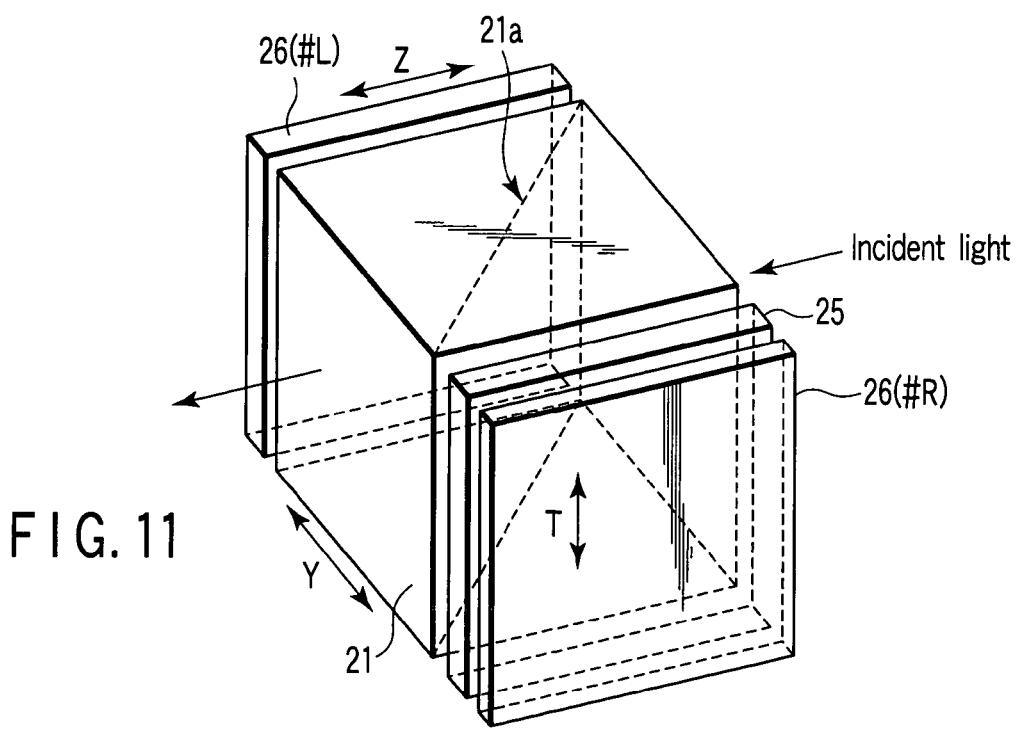
FIG. 11 is a perspective view showing a whole constitution example of another polarized beam splitter in the wiring pattern inspection apparatus according to the second embodiment.

FIG. 11 is a perspective view showing an example of the whole constitution of the polarized beam splitter 21 which brings a similar function.

In the constitution shown in FIG. 11, the polarized beam splitter 21 comprises a polarization film 21a, further a total reflection mirror 26 (#L) is disposed on a side face of the polarization film 21a on a non-reflection face side, and a quarter-wavelength plate 25 and a total reflection mirror 26 (#R) are disposed on the side face of the polarization film 21a on a reflection face side.

That is, when random light is introduced into the polarized beam splitter 21 from the light source 10, a light component Y whose electric-field vector direction is a front/back direction in the figure is extracted from the random light, and guided into the polarized beam splitter 22. On the other hand, at this extraction time, a light component T whose vertical direction in FIG. 2 is an electric-field vector direction escapes from the side face, and is guided into the total reflection mirror 26 (#R) via the quarter-wavelength plate 25.

The total reflection mirror 26 (#R) reflects the light component T whose vertical direction in FIG. 2 guided in this manner is an electric-field vector direction, and accordingly the component is introduced again into the polarized beam splitter 21 via the quarter-wavelength plate 25. Consequently, the light component T which has escaped from the polarized beam splitter 21 and whose vertical direction in FIG. 2 is the electric-field vector direction passes through the quarter-wavelength plate 25 twice, and therefore enters the polarized beam splitter 21 as a light component Z whose electric-field vector direction is a right/left direction in the figure.

Furthermore, the light component Z whose electric-field vector direction is the right/left direction in the figure passes through the polarization film 21a, once goes out of the polarized beam splitter 21, and reaches the total reflection mirror 26 (#L). Moreover, the component is reflected by the total reflection mirror 26 (#L), thereafter enters the polarized beam splitter 21 again, and is reflected by the polarization film 21a. Accordingly, the component is converted into a light component Y whose electric-field vector direction is a front/back direction in the figure, and guided into the polarized beam splitter 22.

Figure 12:
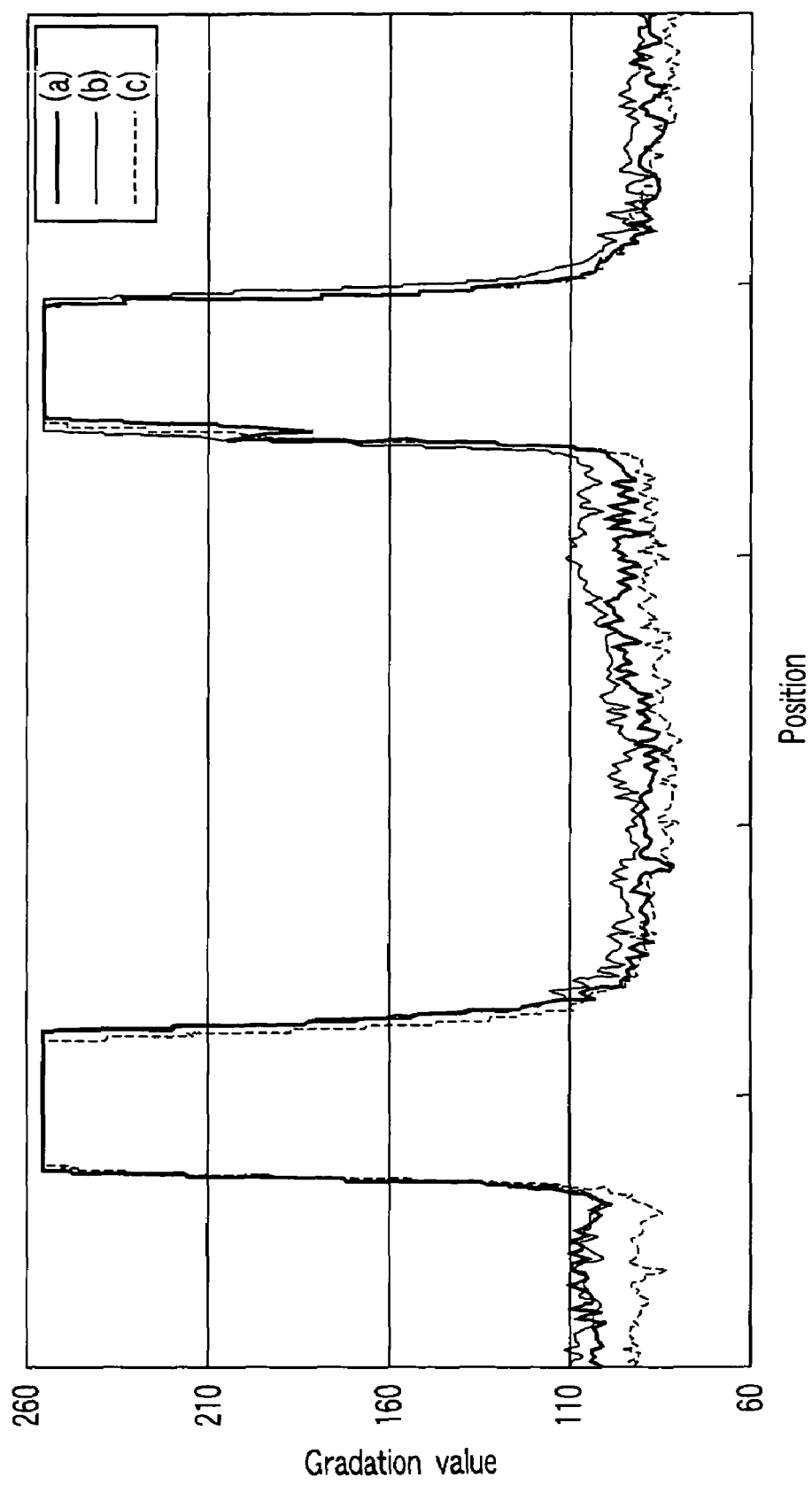
FIG. 12 is a profile diagram showing a gradation difference along an arbitrary line of a wiring pattern portion in image data picked up in a case (a) where a polarized beam splitter is disposed alone, a case (b) where the polarized beam splitter comprises a tab prism and a half-wavelength plate, and a case (c) where the polarized beam splitter comprises a total reflection mirror and a quarter-wavelength plate.

FIG. 12 is a profile diagram showing a gradation difference along an arbitrary line of a wiring pattern portion in image data picked up on the same condition in a case (a) where the polarized beam splitter 21 is disposed alone, a case (b) where the polarized beam splitter 21 comprises a tab prism 23 and a half-wavelength plate 24 as shown in FIG. 10, and a case (c) where the polarized beam splitter 21 comprises a total reflection mirror 26 and a quarter-wavelength plate 25 as shown in FIG. 11.

A difference is hardly seen between (a) and (b), but a contrast enlarging effect (brightness of the wiring pattern portion and insulating layer portion expands) of about 20% at maximum can be confirmed in (a) and (c).

In the wiring pattern inspection apparatus according to the present embodiment, as described above, not only the light component Y extracted by the polarized beam splitter 21 and having the electric-field vector direction which is the front/back direction in the figure, but also the light component Y converted from the light component T whose vertical direction in FIG. 2 is an electric-field vector and having the electric-field vector direction which is the front/back direction in the figure are guided out to the polarized beam splitter 22. Consequently, since the light from the light source 10 can be utilized with good efficiency, light quantity can be increased. As a result, since the contrast difference between the wiring pattern portion and the polyimide insulating layer portion can be expanded, the uppermost-layer wiring pattern can be more clearly imaged.

Third Embodiment

A third embodiment of the present invention will be described with reference to FIGS. 13 to 22B.

The present embodiment relates to improvement of an inspection unit 100 of a wiring pattern inspection apparatus according to the first embodiment. Therefore, here, the inspection unit only will be described.

FIG. 13 is a constitution explanatory view showing one example of the inspection unit of the wiring pattern inspection apparatus according to the present embodiment.

That is, the inspection unit in the wiring pattern inspection apparatus according to the present embodiment comprises a parallel light guiding section 56, a light extraction section 58, a wavelength selection section 60, a work fixing/driving mechanism 50, and a calculation control unit 40.

Furthermore, as shown in FIG. 14, the parallel light guiding section 56 comprises a light source 10, a light guide 11, a hot-wire cut filter 13, a condenser lens 17, a diffusion plate 18, a condenser lens 19, and a fan 20.

The light source 10 may be either high-luminance illumination which emits light over a whole visible range, such as a metal halide lamp, or illumination which emits light having a single wavelength, such as laser.

The light emitted from the light source 10 enters the condenser lens 17 via the light guide 11 and hot-wire cut filter 13. Moreover, this light is converted into uniform parallel light by the condenser lens 17, diffusion plate 18, and condenser lens 19, and thereafter guided into the light extraction section 58. It is to be noted that each of the condenser lenses 17 and 19 is not limited to a single lens, and may be a lens group comprising a plurality of lenses.

The light guided into the light extraction section 58 has to be necessarily uniform parallel light. This is because a characteristic of an optical polarization member used in the light extraction section 58 sensitively depends especially on a light incident angle, and largely influences a desired wavelength characteristic in a case where light other than light having an applied incident angle is incident.

For example, when a polarized beam splitter 68 (described later in detail) is applied to the light extraction section 58, an experiment value of 2% light reduction is obtained in a use wavelength region, when 40° incidence is tried with respect to the polarized beam splitter 68 having this incident angle 45° specification. When 50° incidence is tried, light is reduced by 38%. Accordingly, a gradient curve (shading) having large brightness is generated in an imaging view field.

The image in which this large gradient curve exists is subjected to various image processes, and recognition processes, and this brings an increase of time in a process performed by the calculation control unit 40. Moreover, when the same type of defect exists, for example, in a middle portion and an end portion of the image by presence of the gradient curve, there is a fear that a difference is made in a way to see the defect or contrast of the corresponding portion. Therefore, sufficient attention needs to be paid to constitutions of the condenser lens 17, condenser lens 19, and diffusion plate 18 described later in such a manner that light guided to the light extraction section 58 is necessarily a uniform parallel light.

The diffusion plate 18 needs to be selected especially fully considering heat-resistant temperature, and this diffusion plate 18 fulfills a role of setting an emission light quantity distribution from the light guide 11 to be uniform. A holographic diffuser is an optical member which is most effective as the diffusion plate, but there is difficulty in heat resistance. Therefore, opal is suitable in a case where higher heat resistance is required.

Moreover, in general, a middle portion of the emission light quantity distribution from the end of the light guide 11 tends to be dark. An effect is obtained from an experiment in which a lamp (not shown) in the light source 10 is tilted by an angle of 5 to 6° in order to reduce the tendency that the middle portion is dark.

The fan 20 is disposed instead of the heat radiation mechanism 14 in the first embodiment, and may not be disposed as long as air is sent to the light guide 11 to thereby air-cool the guide and heat measure is not required.

The light extraction section 58 has an erected sectional constitution shown in any of FIGS. 15A to 15D. The section extracts linearly polarized light (front/back direction in the figure is assumed as an electric-field vector direction) from randomly incident light guided from the parallel light guiding section 56, further converts the light into circularly polarized light, and thereafter irradiates the work 51. That is, in FIGS. 15A to 15D, incident light is guided from the right side of the light extraction section 58, and the work 51 disposed under the light extraction section 58 is irradiated with the circularly polarized light.

Figure 15A:
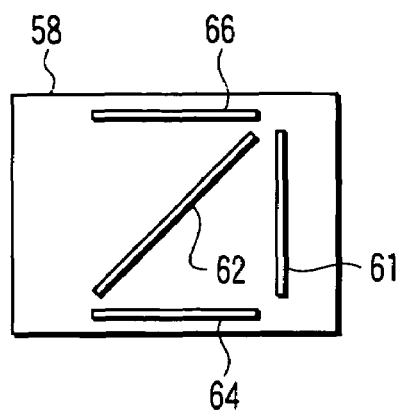
FIG. 15A is a constitution explanatory view showing one example of a light extraction section in the inspection unit of the wiring pattern inspection apparatus according to the third embodiment.

The light extraction section 58 constituted as shown in FIG. 15A comprises: a polarization plate 61 whose transmission axis is in a front/back direction in the figure; a half mirror 62; a quarter-wavelength plate 64; and a polarization plate 66 whose transmission axis is in a right/left direction in the figure. In this case, the polarization plate 61 whose transmission axis is in the front/back direction in the figure extracts a light component whose electric-field vector direction is a front/back direction in the figure from incident light guided from the right side of the figure. The light component whose electric-field vector direction is the front/back direction in the figure is reflected downwards in the figure by the half mirror 62, and thereafter converted into circularly polarized light by the quarter-wavelength plate 64 to irradiate the work 51. This circularly polarized light is reflected by the work 51, and constitutes circularly polarized light whose rotation direction is reversed. This reflected light is converted into a light component whose electric-field vector direction is a right/left direction in the figure by the quarter-wavelength plate 64. Furthermore, after the light passes through the half mirror 62, a ratio of a linearly polarized light component is further increased by the polarization plate 66, and thereafter the light is guided into the wavelength selection section 60.

Figure 15B:
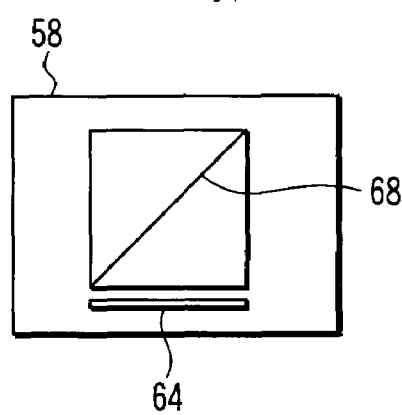
FIG. 15B is a constitution explanatory view showing one example of the light extraction section in the inspection unit of the wiring pattern inspection apparatus according to the third embodiment.

The light extraction section 58 shown in FIG. 15B comprises a polarized beam splitter 68 and a quarter-wavelength plate 64. In this case, the polarized beam splitter 68 extracts a light component whose electric-field vector direction is a front/back direction in the figure from the incident light guided from the right side in the figure, and further the light component whose electric-field vector direction is the front/back direction in the figure is introduced into the quarter-wavelength plate 64. This light component whose electric-field vector direction is the front/back direction in the figure is converted into circularly polarized light by the quarter-wavelength plate 64 to irradiate the work 51. This circularly polarized light is reflected by the work 51, and constitutes circularly polarized light whose rotation direction is reversed. This reflected light is converted into the light component whose electric-field vector direction is a right/left direction in the figure by the quarter-wavelength plate 64. After the light passes through the polarized beam splitter 68, the light is further guided to the wavelength selection section 60.

Figure 15C:
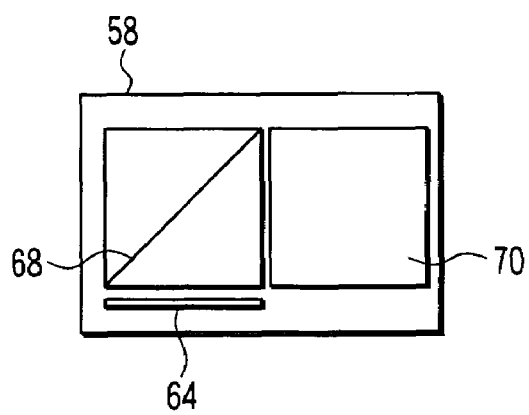
FIG. 15C is a constitution explanatory view showing one example of the light extraction section in the inspection unit of the wiring pattern inspection apparatus according to the third embodiment.

The light extraction section 58 shown in FIG. 15C comprises a polarized beam splitter 70, a polarized beam splitter 68, and a quarter-wavelength plate 64. A positional relation between the polarized beam splitters 70 and 68 is as shown in a perspective view of FIG. 16. In this case, the polarized beam splitter 70 extracts a light component whose electric-field vector direction is a front/back direction in the figure from the incident light guided from the right side in the figure, and further guides the light to the polarized beam splitter 68. The polarized beam splitter 68 reflects this linearly polarized light, and allows the light to enter the quarter-wavelength plate 64. This linearly polarized light is converted into circularly polarized light by the quarter-wavelength plate 64 to irradiate the work 51. This circularly polarized light is reflected by the work 51, and constitutes circularly polarized light whose rotation direction is reversed. This reflected light is converted into a light component whose electric-field vector direction is a right/left direction in the figure by the quarter-wavelength plate 64. After the light passes through the polarized beam splitter 68, the light is further guided to the wavelength selection section 60.

Figure 15D:
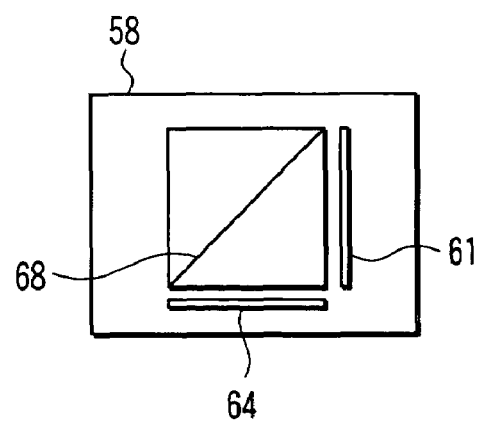
FIG. 15D is a constitution explanatory view showing one example of the light extraction section in the inspection unit of the wiring pattern inspection apparatus according to the third embodiment.

The light extraction section 58 shown in FIG. 15D comprises a polarization plate 61, a polarized beam splitter 68, and a quarter-wavelength plate 64. In this case, the polarization plate 61 extracts a light component whose electric-field vector direction is a front/back direction in the figure from the incident light guided from the right side in the figure, and guides the light to the polarized beam splitter 68. The polarized beam splitter 68 reflects this linearly polarized light, and allows the light to enter the quarter-wavelength plate 64. In this process, impurity components included in the incident light are also removed. Accordingly, the linearly polarized light having higher purity is guided into the quarter-wavelength plate 64.

This linearly polarized light is converted into circularly polarized light by the quarter-wavelength plate 64 to irradiate the work 51. This circularly polarized light is reflected by the work 51, and constitutes circularly polarized light whose rotation direction is reversed. This reflected light is converted into a light component whose electric-field vector direction is a right/left direction in the figure by the quarter-wavelength plate 64. After the light passes through the polarized beam splitter 68, the light is further guided to the wavelength selection section 60.

These polarization plate 61, half mirror 62, quarter-wavelength plate 64, polarization plate 66, polarized beam splitter 68, and polarized beam splitter 70 need to be selected sufficiently considering an applied wavelength region, quenching ratio, polarization ratio, outer shape size capable of irradiating a whole work view field or forming an image and the like. The light of a component with which the work 51 is not irradiated escapes to the side wall in a lens tube depending on the constitution, and therefore a heat-resistant sheet or an air-cooling mechanism is disposed in a side wall portion.

Figure 17:
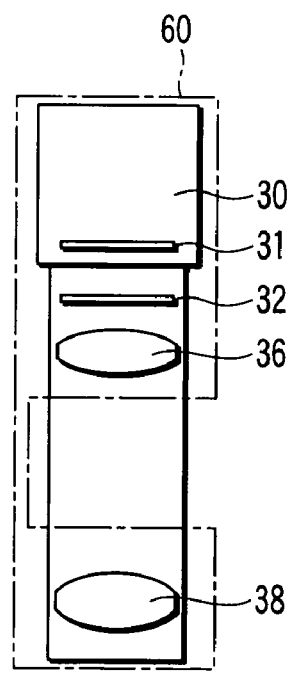
FIG. 17 is a constitution explanatory view showing one example of a wavelength selection section in the inspection unit of the wiring pattern inspection apparatus according to the third embodiment.

As shown in FIG. 17, the wavelength selection section 60 comprises a sensor camera 30, a CCD device 31, a bandpass filter 32, a telecentric image side image forming lens 36, and a telecentric object side image forming lens 38.

That is, the work 51 is irradiated with the circularly polarized light from the light extraction section 58 via the telecentric object side image forming lens 38. Moreover, the reflected light obtained by reflecting the circularly polarized light by the work 51 is converted into a light component whose electric-field vector direction is a right/left direction in the figure by the light extraction section 58 via the telecentric object side image forming lens 38, thereafter constitutes parallel light via the telecentric image side image forming lens 36, passes through the light extraction section 58, and thereafter enters the bandpass filter 32.

It is to be noted that in the present invention, the light with which the work is irradiated is not limited to completely circularly polarized light, and elliptically polarized light may be used as long as the wiring pattern of the uppermost layer of the work is mainly observed.

Next, an operation of the inspection unit of the wiring pattern inspection apparatus according to the present embodiment constituted as described above will be described.

That is, in the inspection unit, when visible light or laser light is emitted from the light source 10, the light is guided into the condenser lens 17 via the light guide 11 and the hot-wire cut filter 13. Furthermore, after the light is converted into uniform parallel light by the condenser lens 17, diffusion plate 18, and condenser lens 19, the light is guided to the light extraction section 58.

Although the light guide 11 is heated by the light from the light source 10, air is sent by the fan 20, and the guide is cooled before reaching temperature at which the function degrades.

The light guided to the light extraction section 58, from which the linearly polarized light (front/back direction in the figure is an electric-field vector direction) is extracted in the light extraction section 58, is further converted into the circularly polarized light to irradiate the work 51.

The work 51 is irradiated with this circularly polarized light via the telecentric object side image forming lens 38, and the light is reflected by the work 51. After passing through the telecentric object side image forming lens 38, the reflected light is converted into a light component whose electric-field vector direction is a right/left direction in the figure by the light extraction section 58, and converted into parallel light via the telecentric image side image forming lens 36. After passing through the polarized beam splitter 22, the light is guided to the bandpass filter 32.

In the bandpass filter 32, a wavelength region in which a difference between an amount of an uppermost-layer wiring pattern by reflected light and that of a polyimide insulating layer portion by reflected light is maximized is extracted, and only light of this wavelength region is introduced into the CCD device 31 in the sensor camera 30. Specifically, in a wavelength of 550 nm which is a green component, reflection spectral sensitivity of the polyimide layer is 0.1%, whereas that of copper is 3%, and 30 times reflection is obtained from an experiment value.

Therefore, when the incident light is imaged by the sensor camera 30, an image of a wiring pattern in which uppermost-layer wiring pattern information is acquired is obtained. That is, since the intensity of the circularly polarized light reflected by the work 51 depends on copper and polyimide, and copper has stronger reflection intensity, the uppermost-layer copper pattern portion is brightly imaged. It is to be noted that when the work 51 is irradiated with the circularly polarized light, the polarization ratio is increased, the wiring pattern and polyimide insulating layer are irradiated, and accordingly the image of the uppermost-layer wiring pattern is more clearly picked up.

This principle will be described with reference to FIGS. 4C and 4D. That is, linearly polarized light $y_1$ whose electric-field vector direction is in the front/back direction in FIG. 2 is extracted, and guided from the light guided by the light guide 11 which guides light L from the light source 10 in parallel via polarization plates or polarized beam splitters combined in many stages. FIGS. 4C and 4D show an example in which the linearly polarized light $y_1$ is extracted and guided by the quarter-wavelength plate 64.

The linearly polarized light $y_1$ passes through the quarter-wavelength plate 64, and is accordingly converted into a circularly polarized light $y_2$ because of the optical characteristic, and a wiring pattern 69 including a base 67 of a polyimide film insulating material is irradiated with this circularly polarized light $y_2$.

As shown in FIG. 4C, when the wiring-pattern 69 of copper or the like is irradiated with this circularly polarized light $y_2$, the incident circularly polarized light $y_2$ is simply reflected as circularly polarized light $y_3$ whose rotation direction is reversed by the surface of the wiring pattern 69 of copper or the like formed by copper plating means or the like. Moreover, when the reflected circularly polarized light $y_3$ passes through the quarter-wavelength plate 64 again, the light is converted into linearly polarized light $y_4$ crossing the incident linearly polarized light $y_1$ at right angles from the optical characteristic. The converted linearly polarized light $y_4$ passes above from the optical characteristic of the polarized beam splitter 21, and is received as a component $y_5$ having uppermost-layer wiring pattern information by the CCD device 31.

Similarly, as shown in FIG. 4D, the transparent base film 67 of a polyimide film insulating material or the like is irradiated with this circularly polarized light $y_2$. It is seen that the transparent base film 67 has anisotropy in the material characteristic. That is, the circularly polarized light $y_2$ introduced into the transparent base film 67 is reflected as elliptically polarized light $y_3'$ whose phase difference has been generated on the surface of the film. Moreover, when the elliptically polarized light $y_3'$ passes through the quarter-wavelength plate 64 again, the light is converted into linearly polarized light $y_4'$ having an azimuth angle in accordance with ellipticity of the elliptically polarized light. This linearly polarized light $y_4'$ hardly passes above because of the optical characteristic of the polarized beam splitter 21 (in actual, an only vector-resolved component $y_5'$ which passes above the polarized beam splitter 21 is transmitted from the component converted into the linearly polarized light $y_4'$ by the quarter-wavelength plate 64). That is, an information component corresponding to the transparent base film 67 of a polyimide film insulating material is hardly guided to the CCD device 31.

Therefore, when information is well extracted in accordance with the material characteristic forming the semiconductor package in this manner, and the light is received by the CCD device 31, any inner-layer wiring pattern is not reflected, and the uppermost-layer wiring pattern information can be picked up as an image having high contrast.

FIG. 18A shows an image showing an example of the uppermost-layer wiring pattern picked up by the sensor camera 30, after acquiring uppermost-layer wiring pattern information by the inspection unit 100, with respect to the multi-layered wiring substrate for the semiconductor package, on which one layer of the inner-layer wiring pattern exists via a polyimide insulating layer with respect to the uppermost-layer wiring pattern. On the other hand, FIG. 18B shows an image showing an example of the uppermost-layer wiring pattern similarly picked up with respect to the multilayered wiring substrate for the semiconductor package, on which three layers of the patterns exist.

As apparent from FIGS. 18A and 18B, even in a case where one layer of inner-layer wiring pattern exists, or three layers exist, it can be confirmed that the only uppermost-layer wiring pattern can be brightly extracted. That is, it is possible to extract the only uppermost-layer wiring pattern regardless of the number of inner layers.

Moreover, FIG. 19A shows an image showing an example of the uppermost-layer wiring pattern obtained by picking up the multilayered wiring substrate for the semiconductor package, on which one layer of the inner-layer wiring pattern exists, by the inspection unit via the polyimide insulating layer with respect to the uppermost-layer wiring pattern. On the other hand, FIG. 19B shows an image obtained by subjecting the image of FIG. 19A to a binarizing process.

As seen from FIG. 19B, when the image picked up by the inspection unit is further subjected to a simple process referred to as binarizing, an uppermost-layer wiring pattern portion is imaged to be brighter, inner-layer pattern and polyimide insulating film portions are imaged to be darker, and an image can be obtained whose uppermost-layer wiring pattern is clarified from another portion. The binarizing has another merit that an image data amount can be reduced, and high-speed image processing is possible.

Moreover, CAD data (pattern design information) or satisfactory work (work in which the wiring pattern is correctly formed) is set as a reference master image in advance, and a portion having a difference can be judged as a defect by comparison with the binarized image, characteristic extraction method or the like.

Furthermore, an image optimum for pattern inspection indicates a state in which a pattern edge is clear and there is not any influence of surface irregularity. A contrast difference between the wiring pattern portion and the polyimide insulating layer portion has to be clearly segmented in order that the pattern edge should be clear. Therefore, a light quantity with which the work is irradiated has to be large, and the work has to be bright in order to eliminate the influence of the wiring pattern surface irregularity.

Figure 16:
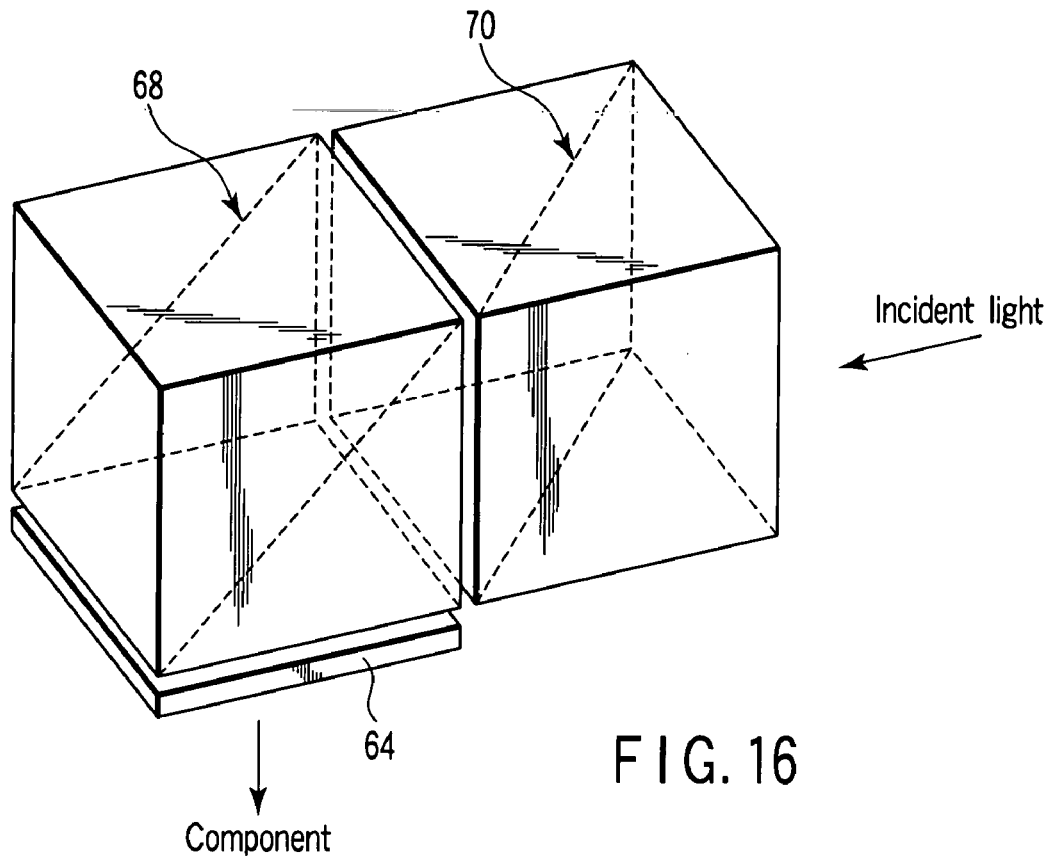
FIG. 16 is a perspective view showing a positional relation between two stages of polarized beam splitters arranged in series.
Figure 20:
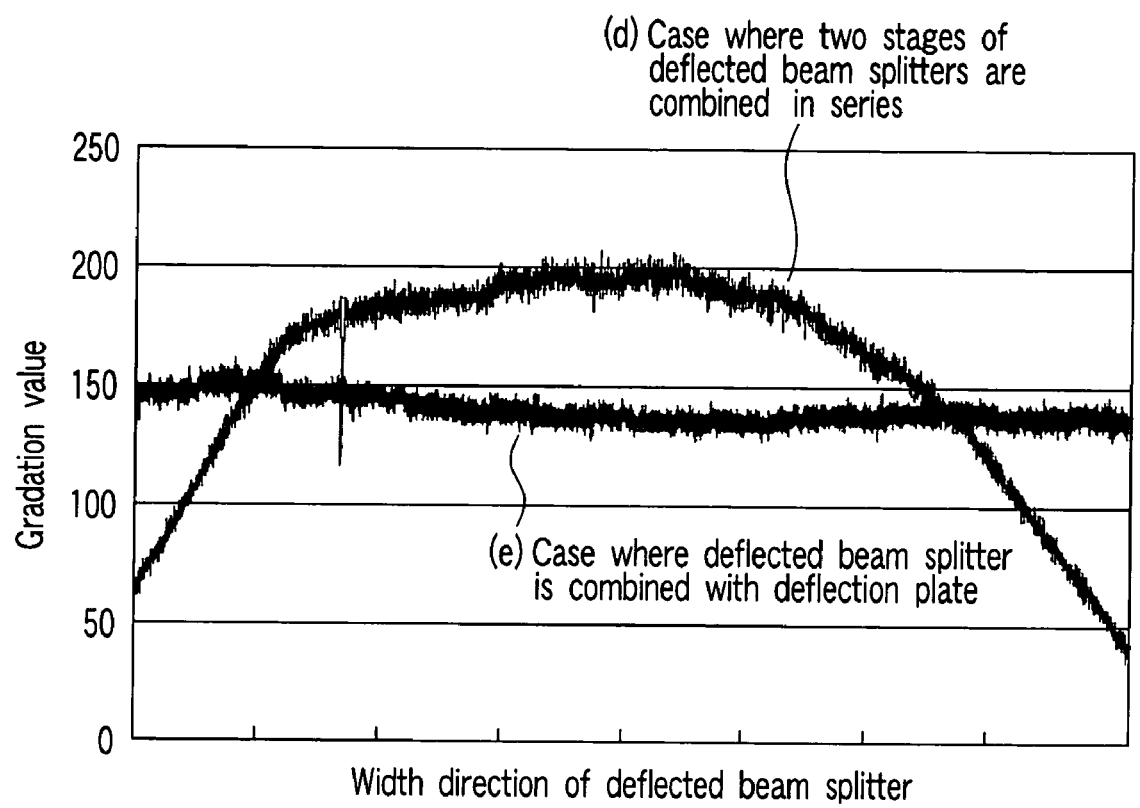
FIG. 20 shows one example of a line profile in an imaging view field width direction in an image in a case where two stages of polarized beam splitters are combined in series, and an image in a case where the polarized beam splitter and a transverse wave polarization plate are combined to raise a polarization efficiency.

FIG. 20 shows one example of a line profile in an imaging view field width direction in a case (curve (d) in the figure) where the polarized beam splitter 70 is combined with the polarized beam splitter 68 in series as shown in FIGS. 15C and 16, and a case (curve (e) in the figure) where the polarized beam splitter 68 is combined with the transverse wave polarization plate 61 as shown in FIG. 15D to raise a polarization efficiency in the light extraction section 58.

Figure 21A:
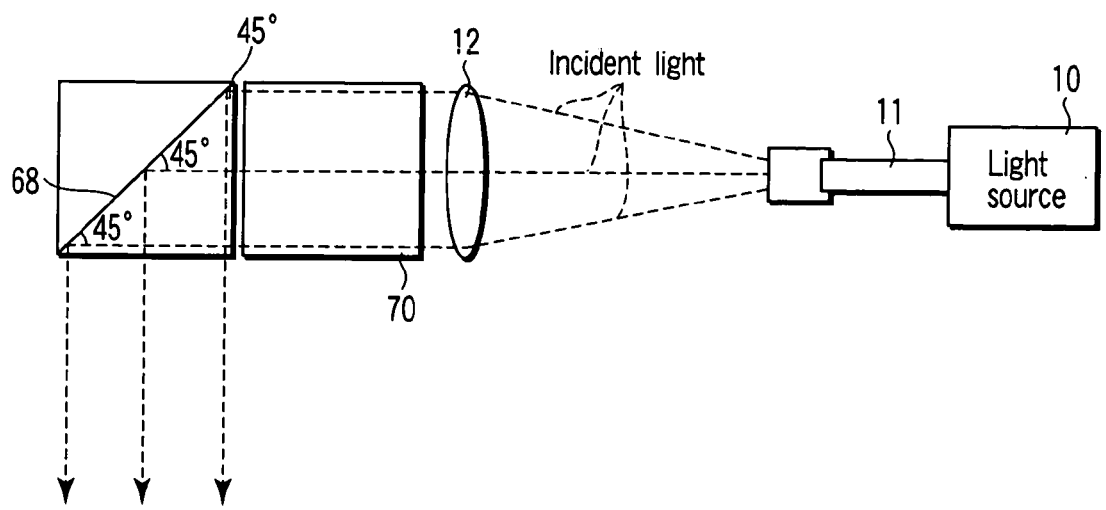
FIG. 21A is a diagram showing a case where there is not any shift from an applied incident angle in opposite end portions of the polarized beam splitter (a case where two stages of the polarized beam splitters are arranged in series).
Figure 21B:
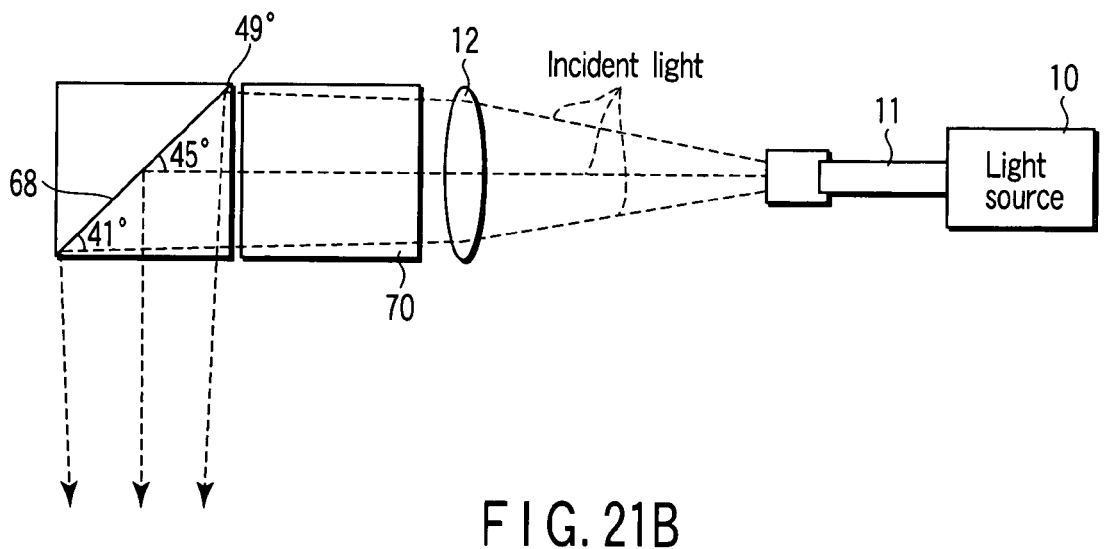
FIG. 21B is an explanatory view of the shift from the applied incident angle in the opposite end portions of the polarized beam splitter (a case where two stages of the polarized beam splitters are arranged in series).

As seen from the curve (d) in the figure, the incident angle of an end portion deviates from 45° with respect to the polarized beam splitter having an incident angle 45° specification. That is, in a case where the polarized beam splitter 70 is combined with the polarized beam splitter 68 in series as shown in FIG. 15C, and completely parallel incident light is not formed by the condenser lens 12 as shown in FIG. 21A, for example, as shown in FIG. 21B, the incident angle deviates from 45° in opposite end portions of the polarized beam splitter 68 (FIG. 21B shows., as one example, a case where the incident light enters an upper end portion of the polarized beam splitter 68 at an angle of 49°, and the incident light enters a lower end portion at an angle of 41°). Opposite sides of an imaging view field width direction are excessively dark by dependence on the incident angle, and it has to be said that the binarizing by a single threshold value is difficult in this state. Shift from the applied incident angle in the opposite end portions increases, when a distance between the condenser lens 12 and the polarized beam splitter 68 increases. Therefore, when the polarized beam splitter 70 is disposed between the condenser lens 12 and the polarized beam splitter 68, the dependence on the incident angle by the shift from the applied incident angle in the opposite end portions tends to be higher.

Figure 22A:
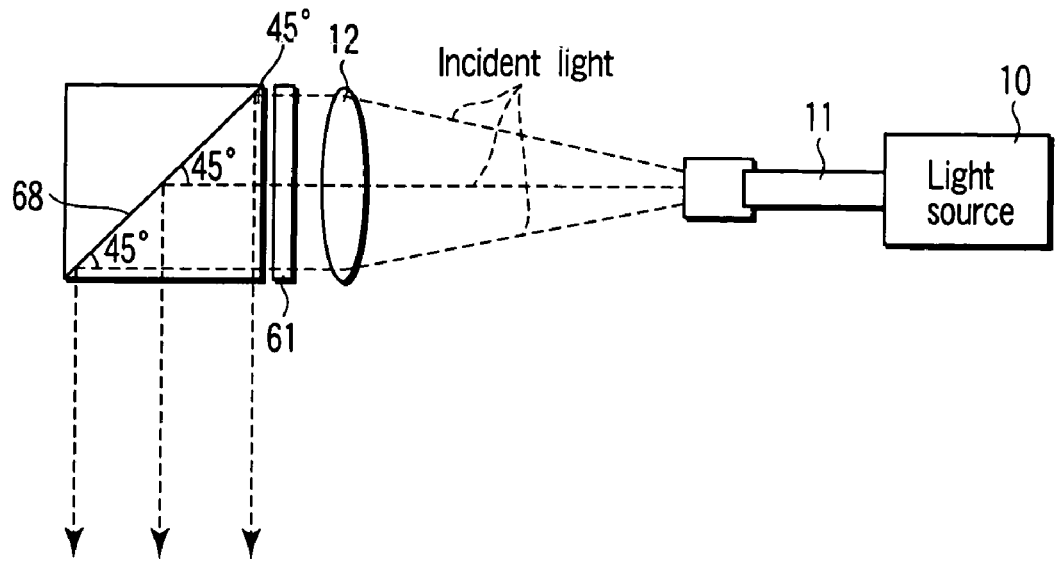
FIG. 22A is a diagram showing a case where there is not any shift from the applied incident angle in the opposite end portions of the polarized beam splitter (case where only one polarized beam splitter is disposed).
Figure 22B:
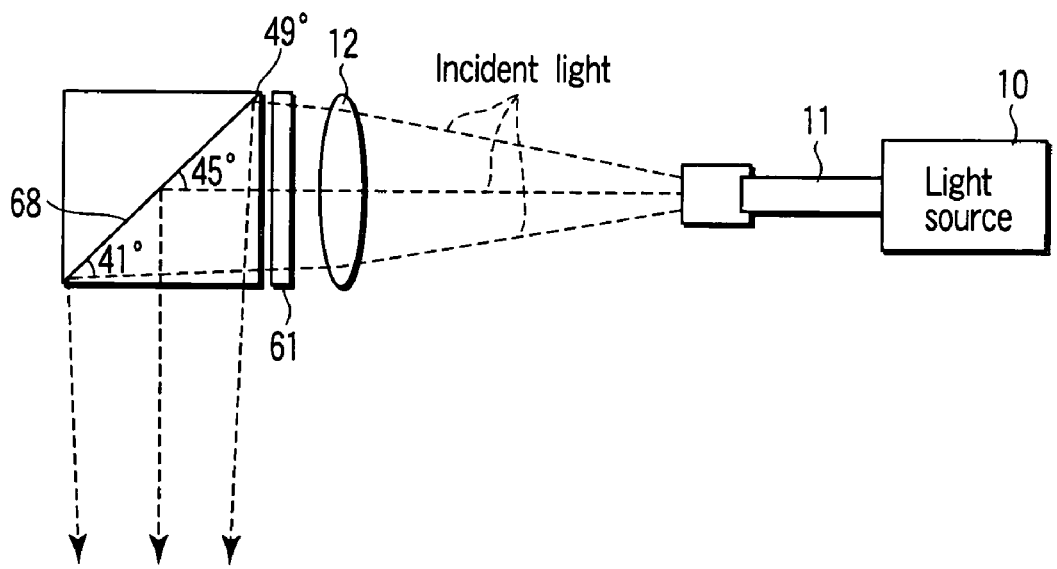
FIG. 22B is an explanatory view of the shift from the applied incident angle in the opposite end portions of the polarized beam splitter (a case where only one polarized beam splitter is disposed).

On the other hand, in a case where the polarization plate 61 thinner than the polarized beam splitter 70 is disposed instead of the polarized beam splitter 70 as shown in FIG. 15D, as shown in FIGS. 22A and 22B, the distance between the condenser lens 12 and the polarized beam splitter 68 can be reduced. Therefore, even if the completely parallel incident light is not formed by the condenser lens 12, the shift from the applied incident angle in the opposite end portions is not very large as compared with the use of the polarized beam splitter 70. Therefore, as seen from the curve (e) in the figure, it is possible to improve the influence of gradation value drop by the shift from the applied incident angle in the opposite end portions by the use of the polarization plate 61. FIG. 22A shows a case where the completely parallel incident light is formed by the condenser lens 12. FIG. 22B shows one example in a case where the completely parallel incident light is not formed by the condenser lens 12, but the shift from the applied incident angle is small in the opposite end portions of the polarized beam splitter 68.

It is to be noted that even if the polarization filter 34 (polarization plate) is used instead of the quarter-wavelength plate in FIGS. 15A to 15D, it is possible to clearly image the only wiring pattern of the uppermost layer.

A best mode for carrying out the present invention has been described above with reference to the accompanying drawings, but the present invention is not limited to such constitution. Any person skilled in the art can think up various modifications and alterations in the scope of invented technical thoughts of patent claims, and it would be understood that these modifications and alterations belong to the technical range of the present invention.

According to the present invention, influence of an inner-layer wiring pattern is optically removed from a multilayered wiring substrate for a semiconductor package, and a highly fine image of an uppermost-layer wiring pattern can be imaged.

As described above, it is possible to realize an inspection apparatus of a wiring pattern, an inspection method, a detection apparatus, and a detection method capable of automatically inspecting the wiring pattern with high reliability.

Moreover, when a line sensor technique is applied to imaging means, an image can be picked up in a short time even with respect to an uppermost-layer wiring pattern having a large area, and the constitution can be simplified.

What is claimed is:

1. A wiring pattern detection apparatus which optically detects an uppermost-layer wiring pattern of a work comprising a multilayered wiring substrate for a semiconductor package having wiring patterns on at least front/back surfaces of a light-transmitting base film, the apparatus comprising:
   a light source;
   parallel light guiding means for guiding light from the light source substantially in parallel;
   first extraction means for extracting first linearly polarized light whose electric-field vector direction crosses a guiding direction of the light at right angles from the light guided by the parallel light guiding means;
   circularly polarized light conversion means for converting the first linearly polarized light extracted by the first extraction means into circularly polarized light;
   irradiation means for irradiating the work with the circularly polarized light converted by the circularly polarized light conversion means;
   second extraction means for extracting second linearly polarized light whose electric-field vector direction crosses the first linearly polarized light at right angles from reflected light obtained by reflecting the circularly polarized light emitted by the irradiation means by the work; and
   image pickup means for imaging the second linearly polarized light extracted by the second extraction means,
   wherein the parallel light guiding means comprises
   a light guide to guide the light from the light source;
   a diffusion plate to diffuse the light from the light source while keeping an intensity distribution to be constant;
   paralleling means for bringing the light diffused by the diffusion plate substantially in parallel; and
   means for guiding the parallel light brought by the paralleling means.

2. A wiring pattern detection apparatus which optically detects an uppermost-layer wiring pattern of a work comprising a multilayered wiring substrate for a semiconductor package having wiring patterns on at least front/back surfaces of a light-transmitting base film, the apparatus comprising:
   a light source;
   parallel light guiding means for guiding light from the light source substantially in parallel;
   a polarized beam splitter to extract first linearly polarized light whose electric-field vector direction crosses a guiding direction of the light at right angles from the light guided by the parallel light guiding means and to guide the extracted first linearly polarized light in the light guiding direction and a direction crossing the direction of the electric-field vector of the first linearly polarized light at right angles;
   a quarter-wavelength plate to convert the first linearly polarized light guided by the polarized beam splitter into circularly polarized light;
   irradiation means for irradiating the work with the circularly polarized light converted by the quarter-wavelength plate; and
   image pickup means,
   wherein the circularly polarized light emitted by the irradiation means is inverted by the work to reverse a rotation direction, and is thereafter transmitted through the quarter-wavelength plate, second linearly polarized light whose electric-field vector direction crosses the first linearly polarized light at right angles is extracted by the polarized beam splitter, and the extracted second linearly polarized light is imaged by the image pickup means, and
   wherein the parallel light guiding means comprises
   a light guide to guide the light from the light source;
   a diffusion plate to diffuse the light from the light source while keeping an intensity distribution to be constant;
   paralleling means for bringing the light diffused by the diffusion plate substantially in parallel; and
   means for guiding the parallel light brought by the paralleling means.

3. A wiring pattern detection apparatus which optically detects an uppermost-layer wiring pattern of a work comprising a multilayered wiring substrate for a semiconductor package having wiring patterns on at least front/back surfaces of a light-transmitting base film, the apparatus comprising:
   a light source;
   parallel light guiding means for guiding light from the light source substantially in parallel;
   a polarization plate to extract first linearly polarized light whose electric-field vector direction crosses a guiding direction of the light at right angles from the light guided by the parallel light guiding means;
   a polarized beam splitter to guide the first linearly polarized light extracted by the polarization plate in the light guiding direction and a direction crossing the direction of the electric-field vector of the first linearly polarized light at right angles;

a quarter-wavelength plate to convert the first linearly polarized light guided by the polarized beam splitter into circularly polarized light;

irradiation means for irradiating the work with the circularly polarized light converted by the quarter-wavelength plate; and image pickup means, wherein the circularly polarized light emitted by the irradiation means is reflected by the work to reverse a rotation direction, and is thereafter transmitted through the quarter-wavelength plate, second linearly polarized light whose electric-field vector direction crosses the first linearly polarized light at right angles is extracted by the polarized beam splitter, and the extracted second linearly polarized light is imaged by the image pickup means, and wherein the parallel light guiding means comprises a light guide to guide the light from the light source;

a diffusion plate to diffuse the light from the light source while keeping an intensity distribution to be constant;

paralleling means for bringing the light diffused by the diffusion plate substantially in parallel; and means for guiding the parallel light brought by the paralleling means.

4. The wiring pattern detection apparatus according to claim 1, further comprising:

an infrared filter to remove an infrared component from the light from the light source and which is disposed between the light source and the light guide, or between the light guide and the diffusion plate.

5. The wiring pattern detection apparatus according to claim 2, further comprising:

an infrared filter to remove an infrared component from the light from the light source and which is disposed between the light source and the light guide, or between the light guide and the diffusion plate.

6. The wiring pattern detection apparatus according to claim 3, further comprising:

an infrared filter to remove an infrared component from the light from the light source and which is disposed between the light source and the light guide, or between the light guide and the diffusion plate.

7. A wiring pattern detection apparatus which optically detects an uppermost-layer wiring pattern of a work comprising a multilayered wiring substrate for a semiconductor package having wiring patterns on at least front/back surfaces of a light-transmitting base film, the apparatus comprising:

a light source;

parallel light guiding means for guiding light from the light source substantially in parallel;

first extraction means for extracting first linearly polarized light whose electric-field vector direction crosses a guiding direction of the light at right angles from the light guided by the parallel light guiding means;

circularly polarized light conversion means for converting the first linearly polarized light extracted by the first extraction means into circularly polarized light;

irradiation means for irradiating the work with the circularly polarized light converted by the circularly polarized light conversion means;

second extraction means for extracting second linearly polarized light whose electric-field vector direction crosses the first linearly polarized light at right angles from reflected light obtained by reflecting the circularly polarized light emitted by the irradiation means by the work;

image pickup means for imaging the second linearly polarized light extracted by the second extraction means; and cooling means for cooling the parallel light guiding means.

8. A wiring pattern detection apparatus which optically detects an uppermost-layer wiring pattern of a work comprising a multilayered wiring substrate for a semiconductor package having wiring patterns on at least front/back surfaces of a light-transmitting base film, the apparatus comprising:

a light source;

parallel light guiding means for guiding light from the light source substantially in parallel;

a polarized beam splitter to extract first linearly polarized light whose electric-field vector direction crosses a guiding direction of the light at right angles from the light guided by the parallel light guiding means and to guide the extracted first linearly polarized light in the light guiding direction and a direction crossing the direction of the electric-field vector of the first linearly polarized light at right angles;

a quarter-wavelength plate to convert the first linearly polarized light guided by the polarized beam splitter into circularly polarized light;

irradiation means for irradiating the work with the circularly polarized light converted by the quarter-wavelength plate;

image pickup means; and cooling means for cooling the parallel light guiding means, wherein the circularly polarized light emitted by the irradiation means is inverted by the work to reverse a rotation direction, and is thereafter transmitted through the quarter-wavelength plate, second linearly polarized light whose electric-field vector direction crosses the first linearly polarized light at right angles is extracted by the polarized beam splitter, and the extracted second linearly polarized light is imaged by the image pickup means.

9. A wiring pattern detection apparatus which optically detects an uppermost-layer wiring pattern of a work comprising a multilayered wiring substrate for a semiconductor package having wiring patterns on at least front/back surfaces of a light-transmitting base film, the apparatus comprising:

a light source;

parallel light guiding means for guiding light from the light source substantially in parallel;

a polarization plate to extract first linearly polarized light whose electric-field vector direction crosses a guiding direction of the light at right angles from the light guided by the parallel light guiding means;

a polarized beam splitter to guide the first linearly polarized light extracted by the polarization plate in the light guiding direction and a direction crossing the direction of the electric-field vector of the first linearly polarized light at right angles;

a quarter-wavelength plate to convert the first linearly polarized light guided by the polarized beam splitter into circularly polarized light;

irradiation means for irradiating the work with the circularly polarized light converted by the quarter-wavelength plate;

image pickup means; and cooling means for cooling the parallel light guiding means, wherein the circularly polarized light emitted by the irradiation means is reflected by the work to reverse a rotation direction, and is thereafter transmitted through the quarter-wavelength plate, second linearly polarized light whose electric-field vector direction crosses the first linearly polarized light at right angles is extracted by the polarized beam splitter, and the extracted second linearly polarized light is imaged by the image pickup means.

10. A wiring pattern detection apparatus which optically detects an uppermost-layer wiring pattern of a work comprising a multilayered wiring substrate for a semiconductor package having wiring patterns on at least front/back surfaces of a light-transmitting base film, the apparatus comprising:
   a light source;
   parallel light guiding means for guiding light from the light source substantially in parallel;
   first extraction means for extracting first linearly polarized light whose electric-field vector direction crosses a guiding direction of the light at right angles from the light guided by the parallel light guiding means;
   circularly polarized light conversion means for converting the first linearly polarized light extracted by the first extraction means into circularly polarized light;
   irradiation means for irradiating the work with the circularly polarized light converted by the circularly polarized light conversion means;
   second extraction means for extracting second linearly polarized light whose electric-field vector direction crosses the first linearly polarized light at right angles from reflected light obtained by reflecting the circularly polarized light emitted by the irradiation means by the work;
   image pickup means for imaging the second linearly polarized light extracted by the second extraction means;
   selection means for selecting a wavelength region in which a difference between an amount of the uppermost-layer wiring pattern by reflected light and that of a pattern other than the uppermost-layer wiring pattern by the reflected light is larger than a predetermined value in the second linearly polarized light; and
   selected wavelength light component guiding means for guiding a light component in the wavelength region selected by the selection means.

11. A wiring pattern detection apparatus which optically detects an uppermost-layer wiring pattern of a work comprising a multilayered wiring substrate for a semiconductor package having wiring patterns on at least front/back surfaces of a light-transmitting base film, the apparatus comprising:
   a light source;
   parallel light guiding means for guiding light from the light source substantially in parallel;
   a polarized beam splitter to extract first linearly polarized light whose electric-field vector direction crosses a guiding direction of the light at right angles from the light guided by the parallel light guiding means and to guide the extracted first linearly polarized light in the light guiding direction and a direction crossing the direction of the electric-field vector of the first linearly polarized light at right angles;
   a quarter-wavelength plate to convert the first linearly polarized light guided by the polarized beam splitter into circularly polarized light;
   irradiation means for irradiating the work with the circularly polarized light converted by the quarter-wavelength plate;
   image pickup means;
   selection means for selecting a wavelength region in which a difference between an amount of the uppermost-layer wiring pattern by reflected light and that of a pattern other than the uppermost-layer wiring pattern by the reflected light is larger than a predetermined value in the second linearly polarized light; and
   selected wavelength light component guiding means for guiding a light component in the wavelength region selected by the selection means,
   wherein the circularly polarized light emitted by the irradiation means is inverted by the work to reverse a rotation direction, and is thereafter transmitted through the quarter-wavelength plate, second linearly polarized light whose electric-field vector direction crosses the first linearly polarized light at right angles is extracted by the polarized beam splitter, and the extracted second linearly polarized light is imaged by the image pickup means.

12. A wiring pattern detection apparatus which optically detects an uppermost-layer wiring pattern of a work comprising a multilayered wiring substrate for a semiconductor package having wiring patterns on at least front/back surfaces of a light-transmitting base film, the apparatus comprising:
   a light source;
   parallel light guiding means for guiding light from the light source substantially in parallel;
   a polarization plate to extract first linearly polarized light whose electric-field vector direction crosses a guiding direction of the light at right angles from the light guided by the parallel light guiding means;
   a polarized beam splitter to guide the first linearly polarized light extracted by the polarization plate in the light guiding direction and a direction crossing the direction of the electric-field vector of the first linearly polarized light at right angles;
   a quarter-wavelength plate to convert the first linearly polarized light guided by the polarized beam splitter into circularly polarized light;
   irradiation means for irradiating the work with the circularly polarized light converted by the quarter-wavelength plate;
   image pickup means;
   selection means for selecting a wavelength region in which a difference between an amount of the uppermost-layer wiring pattern by reflected light and that of a pattern other than the uppermost-layer wiring pattern by the reflected light is larger than a predetermined value in the second linearly polarized light; and
   selected wavelength light component guiding means for guiding a light component in the wavelength region selected by the selection means,
   wherein the circularly polarized light emitted by the irradiation means is reflected by the work to reverse a rotation direction, and is thereafter transmitted through the quarter-wavelength plate, second linearly polarized light whose electric-field vector direction crosses the first linearly polarized light at right angles is extracted by the polarized beam splitter, and the extracted second linearly polarized light is imaged by the image pickup means.

13. The wiring pattern detection apparatus according to claim 10, wherein the selected wavelength light component guiding means comprises at least one or more lenses which guide the light component in the wavelength region selected by the selection means in parallel with the image pickup means.

14. The wiring pattern detection apparatus according to claim 11, wherein the selected wavelength light component guiding means comprises at least one or more lenses which guide the light component in the wavelength region selected by the selection means in parallel with the image pickup means.

15. The wiring pattern detection apparatus according to claim 12, wherein the selected wavelength light component guiding means comprises at least one or more lenses which guide the light component in the wavelength region selected by the selection means in parallel with the image pickup means.

16. The wiring pattern detection apparatus according to claim 10, wherein the base film is formed of a polyimide resin, the wiring pattern is formed of copper, the selection means selects a wavelength region including 550 nm, and the image pickup means comprises a CCD.

17. The wiring pattern detection apparatus according to claim 11, wherein the base film is formed of a polyimide resin, the wiring pattern is formed of copper, the selection means selects a wavelength region including 550 nm, and the image pickup means comprises a CCD.

18. The wiring pattern detection apparatus according to claim 12, wherein the base film is formed of a polyimide resin, the wiring pattern is formed of copper, the selection means selects a wavelength region including 550 nm, and the image pickup means comprises a CCD.

19. A wiring pattern detection method which optically detects an uppermost-layer wiring pattern of a work comprising a multilayered wiring substrate for a semiconductor package having wiring patterns on at least front/back surfaces of a light-transmitting base film, the method comprising:
    guiding light substantially in parallel;
    extracting first linearly polarized light whose electric-field vector direction crosses a guiding direction of the light at right angles from the light guided by the parallel light guiding;
    converting the first linearly polarized light extracted by the first extracting into circularly polarized light;
    irradiating the work with the circularly polarized light converted by the circularly polarized light converting;
    extracting second linearly polarized light whose electric-field vector direction crosses the first linearly polarized light at right angles from reflected light obtained by reflecting the circularly polarized light emitted by the irradiating by the work; and
    imaging the second linearly polarized light extracted by the second extracting,
    wherein the guiding comprises
    diffusing the light while keeping an intensity distribution to be constant;
    bringing the light diffused by the diffusing substantially in parallel; and
    guiding the parallel light from the bringing.

20. A wiring pattern detection method which optically detects an uppermost-layer wiring pattern of a work comprising a multilayered wiring substrate for a semiconductor package having wiring patterns on at least front/back surfaces of a light-transmitting base film, the method comprising:
    guiding light substantially in parallel;
    extracting first linearly polarized light whose electric-field vector direction crosses a guiding direction of the light at right angles from the light guided by the parallel light guiding means by a polarization plate;
    guiding the first linearly polarized light extracted by the polarization plate in the light guiding direction and a direction crossing the direction of the electric-field vector of the first linearly polarized light at right angles using a polarized beam splitter;
    converting the first linearly polarized light guided by the polarized beam splitter into circularly polarized light by a quarter-wavelength plate;
    irradiating the work with the circularly polarized light converted by the quarter-wavelength plate; and
    reflecting the circularly polarized light emitted to the work by the work to reverse a rotation direction, thereafter transmitting the polarized light through the quarter-wavelength plate, and extracting second linearly polarized light whose electric-field vector direction crosses the first linearly polarized light at right angles by the polarized beam splitter to image the extracted second linearly polarized light,
    wherein the guiding comprises
    diffusing the light while keeping an intensity distribution to be constant;
    bringing the light diffused by the diffusing substantially in parallel; and
    guiding the parallel light from the bringing.

21. The wiring pattern detection method according to claim 19, wherein the parallel light guiding further comprises: removing an infrared component from the light before the diffusing.

22. The wiring pattern detection method according to claim 20, wherein the parallel light guiding further comprises: removing an infrared component from the light before the diffusing.

23. A wiring pattern detection method which optically detects an uppermost-layer wiring pattern of a work comprising a multilayered wiring substrate for a semiconductor package having wiring patterns on at least front/back surfaces of a light-transmitting base film, the method comprising:
    guiding light substantially in parallel;
    extracting first linearly polarized light whose electric-field vector direction crosses a guiding direction of the light at right angles from the light guided by the parallel light guiding;
    converting the first linearly polarized light extracted by the first extracting into circularly polarized light;
    irradiating the work with the circularly polarized light converted by the circularly polarized light converting;
    extracting second linearly polarized light whose electric-field vector direction crosses the first linearly polarized light at right angles from reflected light obtained by reflecting the circularly polarized light emitted by the irradiating by the work;
    imaging the second linearly polarized light extracted by the second extracting;
    selecting a wavelength region in which a difference between an amount of the uppermost-layer wiring pattern by reflected light and that of a pattern other than the uppermost-layer wiring pattern by the reflected light is larger than a predetermined value in the second linearly polarized light; and
    guiding a light component in the wavelength region selected by the selecting.

24. A wiring pattern detection method which optically detects an uppermost-layer wiring pattern of a work comprising a multilayered wiring substrate for a semiconductor package having wiring patterns on at least front/back surfaces of a light-transmitting base film, the method comprising:
    guiding light substantially in parallel;
    extracting first linearly polarized light whose electric-field vector direction crosses a guiding direction of the light at right angles from the light from the parallel light guiding by a polarization plate;

guiding the first linearly polarized light extracted by the polarization plate in the light guiding direction and a direction crossing the direction of the electric-field vector of the first linearly polarized light at right angles using a polarized beam splitter;

converting the first linearly polarized light guided by the polarized beam splitter into circularly polarized light by a quarter-wavelength plate;

irradiating the work with the circularly polarized light converted by the quarter-wavelength plate;

reflecting the circularly polarized light emitted to the work by the work to reverse a rotation direction, thereafter transmitting the polarized light through the quarter-wavelength plate, and extracting second linearly polarized light whose electric-field vector direction crosses the first linearly polarized light at right angles by the polarized beam splitter to image the extracted second linearly polarized light;

selecting a wavelength region in which a difference between an amount of the uppermost-layer wiring pattern by reflected light and that of a pattern other than the uppermost-layer wiring pattern by the reflected light is larger than a predetermined value in the second linearly polarized light; and guiding a light component in the wavelength region selected by the selecting.

25. The wire pattern detection method according to claim 23, wherein the base film is formed of a polyimide resin, the wiring pattern is formed of copper, the selecting selects a wavelength region including 550 nm, and the imaging picks up the image by a CCD.

26. The wire pattern detection method according to claim 24, wherein the base film is formed of a polyimide resin, the wiring pattern is formed of copper, the selecting selects a wavelength region including 550 nm, and the second extracting picks up the image by a CCD.

* * * * *